(12) United States Patent
Taguchi et al.

(10) Patent No.: US 7,384,974 B2
(45) Date of Patent: Jun. 10, 2008

(54) 4,5-DIHYDRONAPHTHO[1,2-B]THIOPHENE DERIVATIVE

(75) Inventors: Minoru Taguchi, Tokyo (JP); Ryo Suzuki, Tokyo (JP); Ayako Mikami, Tokyo (JP)

(73) Assignee: Taisha Pharmaceutical Co., Ltd., Tokyo (JP)

( * ) Notice: Subject to any disclaimer, the term of this patent is extended or adjusted under 35 U.S.C. 154(b) by 207 days.

(21) Appl. No.: 10/566,572

(22) PCT Filed: Jul. 30, 2004

(86) PCT No.: PCT/JP2004/010944

§ 371 (c)(1),
(2), (4) Date: Jan. 31, 2006

(87) PCT Pub. No.: WO2005/012284

PCT Pub. Date: Feb. 10, 2005

(65) Prior Publication Data

US 2006/0189678 A1    Aug. 24, 2006

(30) Foreign Application Priority Data

Jul. 31, 2003    (JP)    ............... 2003-204357

(51) Int. Cl.
*A61K 31/381* (2006.01)
*C07D 333/74* (2006.01)
*C07D 495/14* (2006.01)

(52) U.S. Cl. .................. 514/443; 549/42; 549/43; 549/44

(58) Field of Classification Search ............ 549/42, 549/43, 44; 514/443
See application file for complete search history.

(56) References Cited

U.S. PATENT DOCUMENTS 4,797,414 A    1/1989    Rimbault

FOREIGN PATENT DOCUMENTS

JP    61-194081 A    8/1986

OTHER PUBLICATIONS

Kenneth Clarke, et al., Naphtho[1,2-b]thiophene. Part 2. Substitution Reactions of Derivatives with One or More Substituents in the Thiophen Ring and of the 4,5-Dihro-derivative, Journal of the Chemical Society, Perkin Transactions I: Organic and Bio-Organic Chemistry, 1977, No. 1, pp. 63-68.

*Primary Examiner*—Bernard Dentz
(74) *Attorney, Agent, or Firm*—Sughrue Mion, PLLC

(57) ABSTRACT

A 4,5-dihydronaphtho[1,2-b]thiophene derivative expressed by the formula:

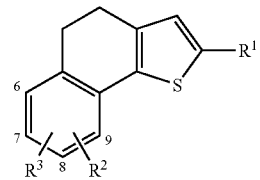

(wherein $R^1$ is a $C_1$ to $C_{10}$ 1-hydroxyalkyl group or a $C_1$ to $C_{10}$ acyl group, and $R^2$ and $R^3$ separately substitute in the 6-, 7-, 8-, or 9-positions, and are each independently a hydrogen atom, a halogen atom, a $C_1$ to $C_{10}$ alkyl group, a hydroxy group, a $C_1$ to $C_{10}$ alkoxy group, a $C_1$ to $C_5$ alkenyloxy group, a $C_1$ to $C_5$ alkynyloxy group, a benzyloxy group, or the like, provided that when $R^1$ is an acyl group and $R^2$ is a hydrogen atom, then $R^3$ is neither a hydrogen atom nor an acetyl group), or a pharmaceutically acceptable salt thereof This is a novel compound that is effective in reducing triglyceride levels in the liver and reducing blood glucose levels.

9 Claims, No Drawings

US 7,384,974 B2

4,5-DIHYDRONAPHTHO[1,2-B]THIOPHENE DERIVATIVE

This is a U.S. national stage entry of Application No. PCT/JP2004/010944 filed Jul. 30, 2004.

TECHNICAL FIELD

This invention relates to a novel 4,5-dihydronaphtho[1,2-b]thiophene derivative, and more particularly relates to a novel 4,5-dihydronaphtho[1,2-b]thiophene derivative that is effective in reducing triglyceride levels in the liver and reducing blood glucose levels, and is useful as a drug for preventing or treating diabetes, hyperlipidemia, fatty liver, obesity, impaired glucose tolerance, diabetes complications (such as kidney disease, neuropathy, and retinopathy), metabolic syndrome, and syndrome X.

BACKGROUND ART

Diabetes is a chronic disease symptomized by high blood glucose due to impaired insulin secretion or impaired insulin action. Over 90% of diabetes is type 2 diabetes, which is categorized as a lifestyle disease, and is most often accompanied by abnormal lipid metabolism (like obesity or hyperlipidemia). The pathophysiology of diabetes such as hyperinsulinemia is a vicious cycle in which the release of VLDL and the synthesis of triglycerides in the liver is accelerated, hyperlipidemia worsens, and an increase in triglycerides or free fatty acids caused by abnormal lipid metabolism further compromises insulin action. Consequently, hypoglycemic drugs and antilipemic drugs are often taken together.

Drugs that work to lower triglyceride levels include nicotinic acid drugs and fibrate-based drugs. It is known, however, that nicotinic acid lowers glucose tolerance, and as for fibrate drugs, while Bezafibrate does improve insulin resistance and thereby strengthens the hypoglycemic action of concurrently used drugs such as sulfonylurea-based drugs, it does not itself exhibit any hypoglycemic action.

Compounds that have a hypoglycemic action include sulfonylurea-based drugs, thiazolidine derivatives, biguanide, α-glucosidase inhibitors, and so on, but other than thiazolidine derivatives don't acts on lipids.

It is stated in the Patent Document 1 that a 4,5-dihydronaphtho[1,2-b]thiophene derivative that is a compound whose structure is similar to that of the compound of the present invention is effective-in the treatment of respiratory disorders, immunoregulation, the treatment of acute tumor diseases, antiedema treatment, the treatment of venous disorders, and so on. However, the compound of the present invention is not mentioned, nor is there any mention of the action of lowering triglyceride levels in the liver or the action of lowering blood glucose levels.

Patent Document 1: Japanese Laid-Open Patent Application No. S61-194081

DISCLOSURE OF THE INVENTION

It is an object of the present invention to provide a novel compound that is effective in reducing triglyceride levels in the liver and reducing blood glucose levels, and more particularly, to provide a compound that is useful as a drug for preventing or treating diabetes, hyperlipidemia, fatty liver, obesity, impaired glucose tolerance, diabetes complications (such as kidney disease, neuropathy, and retinopathy), metabolic syndrome, and syndrome X.

As a result of diligent research aimed at achieving the stated object, the inventors completed the present invention upon discovering that a certain type of 4,5-dihydronaphtho[1,2-b]thiophene derivative suppresses triglyceride production in the liver and lowers blood glucose levels.

Specifically, the present invention directs to:

1. A 4,5-dihydronaphtho[1,2-b]thiophene derivative expressed by the formula:

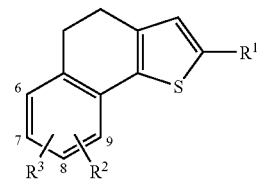

(wherein $R^1$ is a $C_1$ to $C_{10}$ 1-hydroxyalkyl group or a $C_1$ to $C_{10}$ acyl group, and $R^2$ and $R^3$ separately substitute in the 6-, 7-, 8-, or 9-positions, and are each independently a hydrogen atom, a halogen atom, a $C_1$ to $C_{10}$ alkyl group, a hydroxy group, a $C_1$ to $C_{10}$ alkoxy group, a $C_1$ to $C_5$ alkenyloxy group, a $C_1$ to $C_5$ alkynyloxy group, a benzyloxy group, a nitro group, or a group expressed by the formula —$NR^4R^5$ (wherein $R^4$ and $R^5$ are each independently a hydrogen atom, an acetyl group, a trifluoroacetyl group, a $C_1$ to $C_{10}$ alkyl group, or a benzyl group), or $R^2$ and $R^3$ are bonded together to form an ethylenedioxy group, provided that when $R^1$ is an acyl group and $R^2$ is a hydrogen atom, then $R^3$ is neither a hydrogen atom nor an acetyl group), or a pharmaceutically acceptable salt thereof.

2. A pharmaceutical composition comprising the 4,5-dihydronaphtho[1,2-b]thiophene derivative expressed by the above formula or pharmaceutically acceptable salt thereof.

3. A hypotriglyceridemic agent whose active ingredient is the 4,5-dihydronaphtho[1,2-b]thiophene derivative expressed by the above formula or pharmaceutically acceptable salt thereof.

4. A hypoglycemic agent whose active ingredient is the 4,5-dihydronaphtho[1,2-b]thiophene derivative expressed by the above formula or pharmaceutically acceptable salt thereof.

5. An agent for preventing or treating diabetes, hyperlipidemia, fatty liver, obesity, impaired glucose tolerance, diabetes complications, metabolic syndrome, and syndrome X, whose active ingredient is the 4,5-dihydronaphtho[1,2-b]thiophene derivative expressed by the above formula or pharmaceutically acceptable salt thereof.

The compound of the present invention is effective in reducing triglyceride levels in the liver and reducing blood glucose levels, and is useful as a drug for preventing or treating diabetes, hyperlipidemia, fatty liver, obesity, impaired glucose tolerance, diabetes complications (such as kidney disease, neuropathy, and retinopathy), metabolic syndrome, and syndrome X.

BEST MODE FOR CARRYING OUT THE INVENTION

In the present invention, "$C_1$ to $C_{10}$ 1-hydroxyalkyl group" indicates a linear, branched, or cyclic $C_1$ to $C_{10}$ 1-hydroxyalkyl group, examples of which include a hydroxymethyl group, 1-hydroxyethyl group, 1-hydroxypropyl group, 1-hydroxybutyl group, 1-hydroxyisobutyl group, cyclopentyl-hydroxymethyl group, and cyclohexyl-hydroxymethyl group. The "$C_1$ to $C_{10}$ acyl group" indicates a linear, branched, or cyclic $C_1$ to $C_{10}$ acyl group, examples of which include a formyl group, acetyl group, propionyl group, butyryl group, isobutyryl group, cyclopentylcarbonyl group, and cyclohexylcarbonyl group. The "$C_1$ to $C_{10}$ alkyl group" indicates a linear, branched, or cyclic $C_1$ to $C_{10}$ alkyl group, examples of which include a methyl group, ethyl group, propyl group, t-butyl group, cyclopentyl group, cyclohexyl group, and cyclohexylmethyl group. The "$C_1$ to $C_{10}$ alkoxy group" indicates a linear, branched, or cyclic $C_1$ to $C_{10}$ alkoxy group, examples of which include a methoxy group, ethoxy group, propoxy group, t-butoxy group, cyclopentyloxy group, cyclohexyloxy group, and cyclohexylmethyloxy group. The "$C_1$ to $C_5$ alkenyloxy group" indicates a linear or branched $C_1$ to $C_5$ alkenyloxy group, examples of which include a vinyloxy group, allyloxy group, isopropenyloxy group, and 2-isobutenyloxy group. The "$C_1$ to $C_5$ alkynyloxy group" indicates a linear or branched $C_1$ to $C_5$ alkenyloxy group, examples of which include an ethynyloxy group and a 2-propynyloxy group.

Examples of pharmaceutically acceptable salts in the present invention include salts of mineral acids such as sulfuric acid, hydrochloric acid, and phosphoric acid, and salts of organic acids such as acetic acid, oxalic acid, lactic acid, tartaric acid, fumaric acid, maleic acid, methanesulfonic acid, and benzenesulfonic acid.

The compound of the present invention may be a single compound or a mixture of steric isomers.

The compound of the present invention can be manufactured, for example, by the following method.

In this Specification, WSC.HCl stands for 1-ethyl-3-(3-dimethylaminopropyl)carbodiimide hydrochloride, DCC stands for dicyclohexylcarbodiimide, and HOBt stands for 1-hydroxybenzotriazole.

A compound 5a of the present invention, expressed by the above formula, in which $R^1$ is a $C_1$ to $C_{10}$ acyl group, $R^2$ and $R^3$ each independently substitute in the 6-, 7-, 8-, or 9-positions, $R^2$ is a halogen atom, a $C_1$ to $C_{10}$ alkyl group, a $C_1$ to $C_{10}$ alkoxy group, a $C_1$ to $C_5$ alkenyloxy group, a $C_1$ to $C_5$ alkynyloxy group, a benzyloxy group, or a nitro group, and $R^3$ is a hydrogen atom, a halogen atom, a $C_1$ to $C_{10}$ alkyl group, a $C_1$ to $C_{10}$ alkoxy group, a $C_1$ to $C_5$ alkenyloxy group, a $C_1$ to $C_5$ alkynyloxy group, a benzyloxy group, or a nitro group, or $R^2$ and $R^3$ are bonded together to form an ethylenedioxy group, can be synthesized by a method A or B from a tetralone derivative 2a as shown by a reaction scheme 1-4. The tetralone derivative 2a can be synthesized from a carboxylic acid derivative 1a or 1b.

Specifically, substituted benzene and anhydrous succinic anhydride are subjected to a Friedel-Crafts' reaction, and then the ketone is reduced to obtain a carboxylic acid derivative 1a. The reductant used here can be triethylsilane, hydrazine, zinc amalgam, or the like. Substituted bromobenzene is subjected to tributyltin conversion, and subjected to Stille coupling with methyl-4-bromocrotonate, after which the ester is hydrolyzed, and the double bonds are hydrogenated to obtain a carboxylic acid derivative 1b. Substituted benzaldehyde is subjected to a Homer-Emmons reaction with triethyl phosphonoacetate, and then the double bonds are hydrogenated and the ester is reduced, and then the hydroxy groups are mesylated and subjected to nitrile substitution, after which the nitrile is hydrolyzed to obtain a carboxylic acid derivative 1b. The reductant of the ester here can be aluminum lithium hydride, aluminum diisobutyl hydride, diborane, or the like. After that, the carboxylic acid derivative 1a or 1b is converted into an acid chloride, and an intramolecular Friedel-Crafts' reaction is conducted to obtain a tetralone derivative 2a.

With method A, the tetralone derivative 2a is subjected to a Vilsmeier reaction and converted into a chloroformyl derivative, after which the chloroformyl derivative is reacted with ethyl thioglycolate to obtain a thiophene derivative 3a. Next, the ester is hydrolyzed, and the product is converted into an amide to obtain a compound 4a. The method for converting products into an amide here can be a method involving the use of condensing agent such as WSC-HCl, DCC, a method that goes through an acid chloride and so on. Next, the compound obtained here is alkylated to obtain the compound 5a of the present invention. The alkylation agent used here can be a Grignard reagent such as methyl magnesium bromide, or an alkyl metal such as methyl lithium.

With method B, the tetralone derivative 2a is subjected to a Vilsmeier reaction and converted into a chloroformyl derivative, after which this is reacted with an alkyl mercaptomethyl ketone in the presence of a base to obtain the compound 5a of the present invention.

Reaction Scheme 1-1

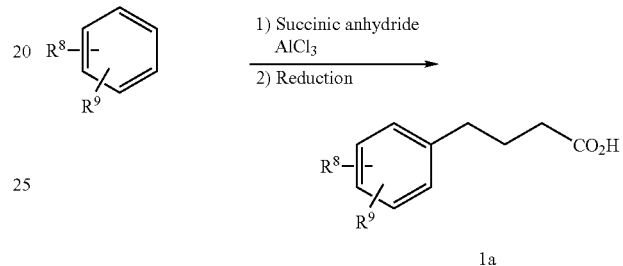

(wherein, $R^8$ is a halogen atom, a $C_1$ to $C_{10}$ alkyl group, a $C_1$ to $C_5$ alkenyl group, a $C_1$ to $C_5$ alkynyl group, a $C_1$ to $C_{10}$ alkoxy group, or a benzyloxy group, and $R^9$ is a hydrogen atom, a halogen atom, a $C_1$ to $C_{10}$ alkyl group, a $C_1$ to $C_5$ alkenyl group, a $C_1$ to $C_5$ alkynyl group, a $C_1$ to $C_{10}$ alkoxy group, or a benzyloxy group, or $R^8$ and $R^9$ are bonded together to form an ethylenedioxy group.)

Reaction Scheme 1-2

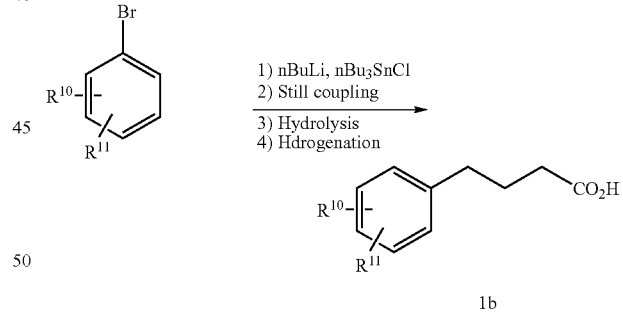

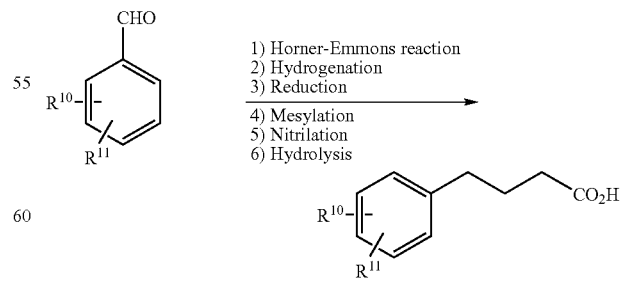

(wherein, $R^{10}$ is a halogen atom, a $C_1$ to $C_{10}$ alkyl group, a $C_1$ to $C_5$ alkenyl group, a $C_1$ to $C_5$ alkynyl group, a $C_1$ to $C_{10}$ alkoxy group, a benzyloxy group, or a nitro group, and $R^{11}$ is a hydrogen atom, a halogen atom, a $C_1$ to $C_{10}$ alkyl group, a $C_1$ to $C_5$ alkenyl group, a $C_1$ to $C_5$ alkynyl group, a $C_1$ to $C_{10}$ alkoxy group, a benzyloxy group, or a nitro group, or $R^{10}$ and $R^{11}$ are bonded together to form an ethylenedioxy group.)

Reaction Scheme 1-3

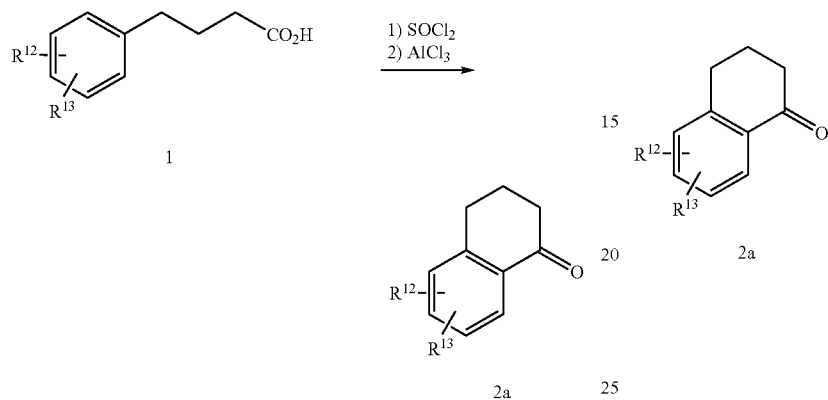

(wherein, $R^{12}$ is a halogen atom, a $C_1$ to $C_{10}$ alkyl group, a $C_1$ to $C_5$ alkenyl group, a $C_1$ to $C_5$ alkyn group, a $C_1$ to $C_{10}$ alkoxy group, a benzyloxy group, or a nitro group, and $R^{13}$ is a hydrogen atom, a halogen atom, a $C_1$ to $C_{10}$ alkyl group, a $C_1$ to $C_5$ alkenyl group, a $C_1$ to $C_5$ alkynyl group, a $C_1$ to $C_{10}$ alkoxy group, a benzyloxy group, or a nitro group, or $R^{12}$ and $R^{13}$ are bonded together to form an ethylenedioxy group.)

Reaction Scheme 1-4

Method A

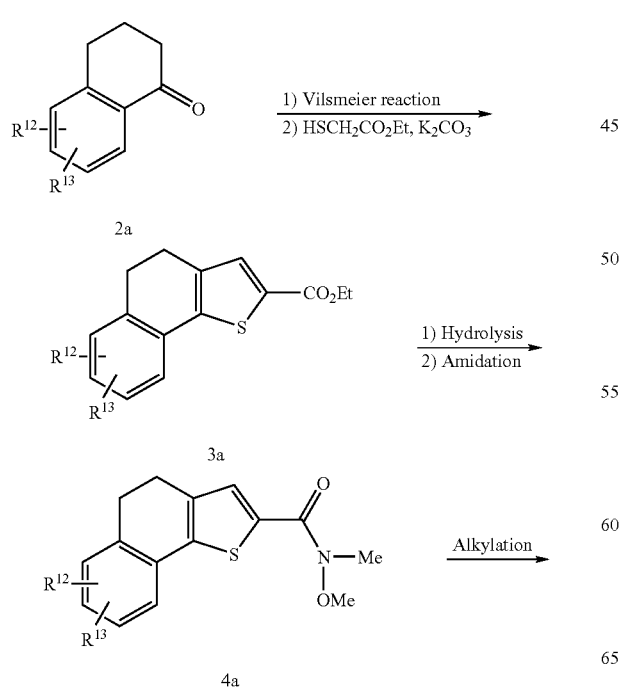

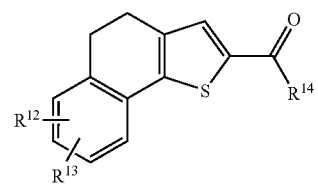

Method B

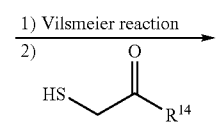

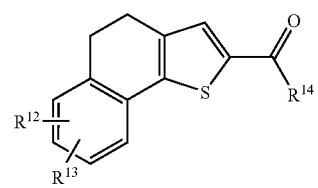

(wherein, $R^{12}$ and $R^{13}$ are defined the same as above, and $R^{14}$ is a $C_1$ to $C_{10}$ alkyl group.)

A compound 5b of the present invention, in which $R^1$ is a $C_1$ to $C_{10}$ acyl group, $R^2$ and $R^3$ separately substitute in the 6-, 7-, 8-, or 9-positions, $R^2$ is a hydroxy group, and $R^3$ is a hydrogen atom or a hydroxy group, can be obtained by the debenzylation of a compound 5c, in which $R^1$ is a $C_1$ to $C_{10}$ acyl group, $R^2$ and $R^3$ separately substitute in the 6-, 7-, 8-, or 9-positions, $R^2$ is a benzyloxy group, and $R^3$ is a hydrogen atom or a benzyloxy group, as shown by a reaction scheme 2. Examples of the debenzylation method here include hydrogenation with palladium-carbon, and the use of trimethylsilyl iodide, boron trifluoride, or ethanethiol.

Reaction Scheme 2

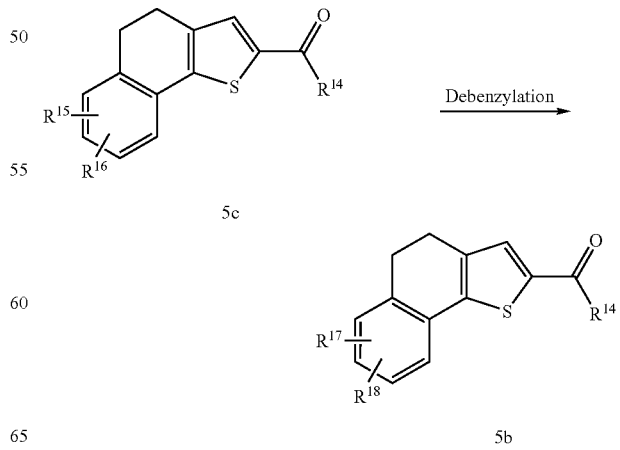

(wherein, $R^{14}$ is defined the same as above, $R^{15}$ is a benzyloxy group, $R^{16}$ is a hydrogen atom or a benzyloxy group, $R^{17}$ is a hydroxy group, and $R^{18}$ is a hydrogen atom or a hydroxy group.)

As shown in a reaction scheme 3, the compound 5b can be obtained by the demethylation of a compound 5d, in which $R^1$ is a $C_1$ to $C_{10}$ acyl group, $R^2$ and $R^3$ separately substitute in the 6-, 7-, 8-, or 9-positions, $R^2$ is a methoxy group, and $R^3$ is a hydrogen atom or a methoxy group. Examples of the demethylation method here include the use of trimethylsilane iodide, sodium thioethoxide, boron trifluoride, or the like.

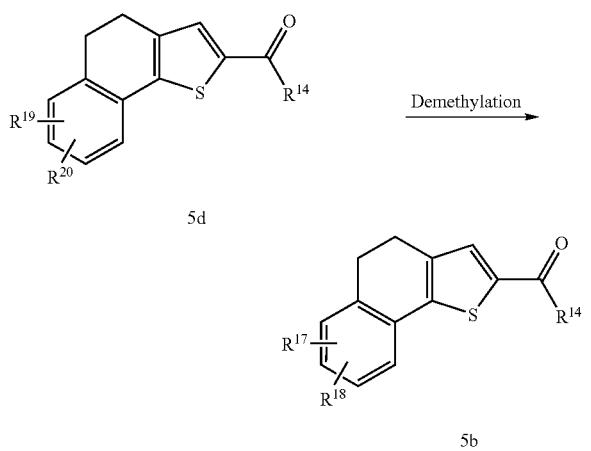

Reaction Scheme 3

5d

5b (wherein, $R^{14}$, $R^{17}$, and $R^{18}$ are defined the same as above, $R^{19}$ is a methoxy group, and $R^{20}$ is a hydrogen atom or a methoxy group.)

As shown in a reaction scheme 4, the compound 5b can also be obtained by the hydrolysis and debenzoylation of a compound 5e, in which $R^1$ is a $C_1$ to $C_{10}$ acyl group, $R^2$ and $R^3$ separately substitute in the 6-, 7-, 8-, or 9-positions, $R^2$ is a benzoyloxy group, and $R^3$ is a hydrogen atom or a benzoyloxy group.

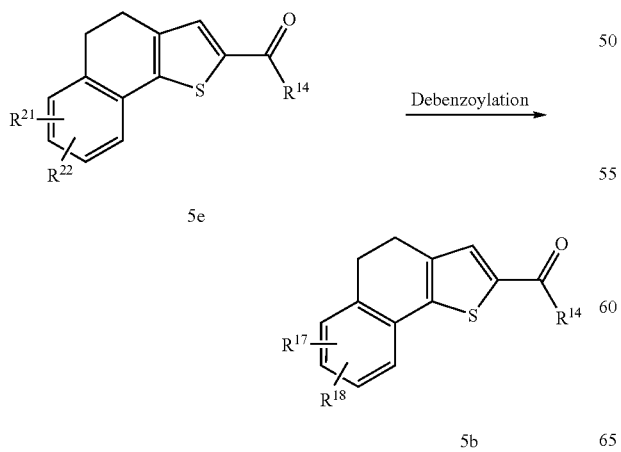

Reaction Scheme 4

5e

5b (wherein, $R^{14}$, $R^{17}$, and $R^{18}$ are defined the same as above, $R^{21}$ is a benzoyloxy group, and $R^{22}$ is a hydrogen atom or a benzoyloxy group.)

A compound 5f of the present invention, in which $R^1$ is a $C_1$ to $C_{10}$ acyl group, $R^2$ and $R^3$ separately substitute in the 6-, 7-, 8-, or 9-positions, $R^2$ is a group expressed by the formula —$NR^{23}R^{24}$ (wherein $R^{23}$ and $R^{24}$ are each independently a $C_1$ to $C_{10}$ alkyl group or a benzyl group), and $R^3$ is a hydrogen atom or a group expressed by the formula —$NR^{23}R^{24}$ (wherein $R^{23}$ and $R^{24}$ are each independently a $C_1$ to $C_{10}$ alkyl group or a benzyl group), can be synthesized from a nitro compound 3b as shown by a reaction scheme 5-1. Examples of the method for reducing the nitro group here include hydrogenation with palladium-carbon, and the use of iron, zinc, tin, or the like.

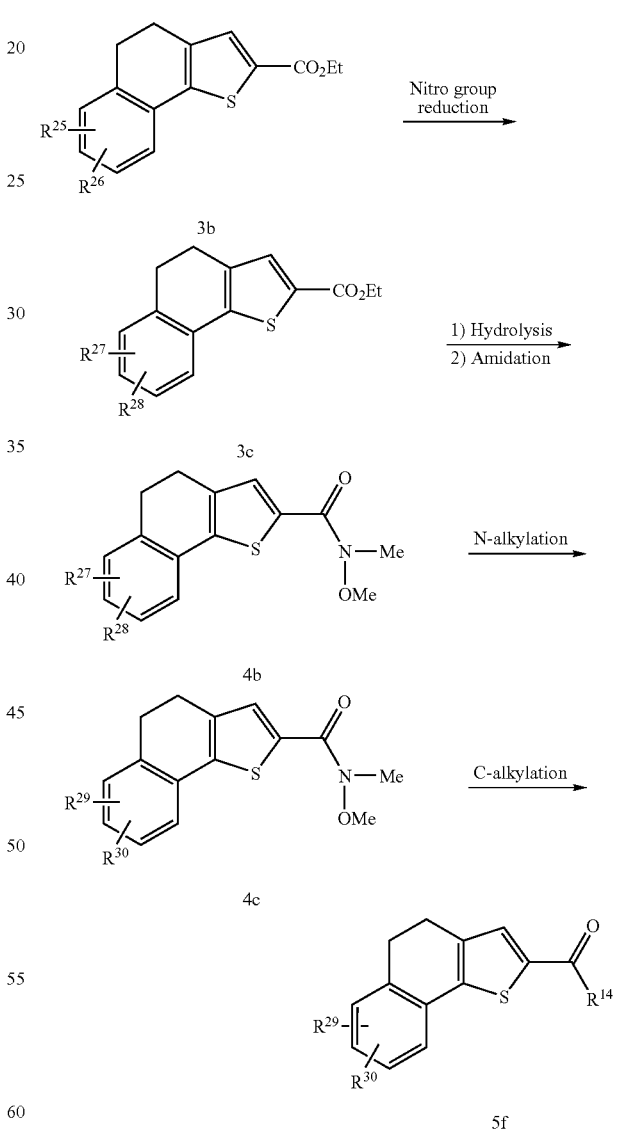

Reaction Scheme 5-1

3b

3c

4b

4c

5f (wherein, $R^{14}$ is defined the same as above, $R^{25}$ is a nitro group, $R^{26}$ is a hydrogen atom or a nitro group, $R^{27}$ is an amino group, $R^{28}$ is a hydrogen atom or an amino group, $R^{29}$ is a group expressed by the formula —$NR^{23}R^{24}$ (wherein $R^{23}$ and $R^{24}$ are defined the same as above), $R^{30}$ is a hydrogen atom or a group expressed by the formula —NR$^{23}$R$^{24}$ (wherein R$^{23}$ and R$^{24}$ are defined the same as above), and R$^{23}$ and R$^{24}$ are each independently a C$_1$ to C$_{10}$ alkyl group or a benzyl group.)

As shown in a reaction scheme 5-2, the compound 5f can be obtained by first hydrolyzing and then N-alkylating a compound 5g in which R$^1$ is a C$_1$ to C$_{10}$ acyl group, R$^2$ and R$^3$ separately substitute in the 6-, 7-, 8-, or 9-positions, R$^2$ is a trifluoroacetamide group, and R$^3$ is a hydrogen atom or a trifluoroacetamide group.

Reaction Scheme 5-2

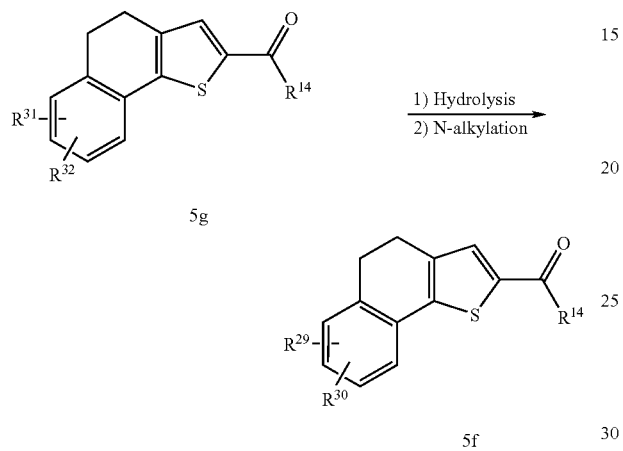

5g

5f (wherein, R$^{14}$, R$^{29}$, and R$^{30}$ are defined the same as above, R$^{31}$ is a trifluoroacetamide group, and R$^{32}$ is a hydrogen atom or a trifluoroacetamide group.)

A compound 5h of the present invention, in which R$^1$ is a C$_1$ to C$_{10}$ acyl group, R$^2$ and R$^3$ separately substitute in the 6-, 7-, 8-, or 9-positions, R$^2$ is a group expressed by the formula —NR$^{33}$R$^{34}$ (wherein R$^{33}$ is a C$_1$ to C$_{10}$ alkyl group or a benzyl group, and R$^{34}$ is a hydrogen atom), and R$^3$ is a hydrogen atom or a group expressed by the formula —NR$^{33}$R$^{34}$ (wherein R$^{33}$ is a C$_1$ to C$_{10}$ alkyl group or a benzyl group, and R$^{34}$ is a hydrogen atom), can be synthesized from a compound 4b as shown by a reaction scheme 6-1. Here, a compound 4d can also be obtained by a method in which imination is followed by reduction.

Reaction Scheme 6-1

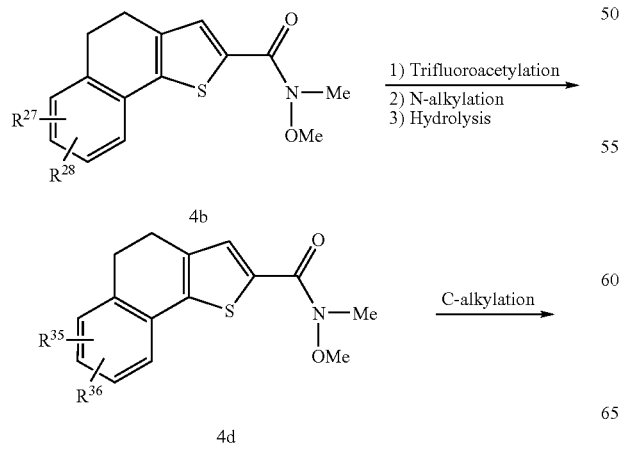

4b

4d

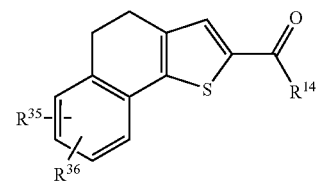

5h (wherein, R$^{14}$, R$^{27}$, and R$^{28}$ are defined the same as above, R$^{35}$ is a group expressed by the formula —NR$^{33}$R$^{34}$ (wherein R$^{33}$ and R$^{34}$ are defined the same as above), and R$^{36}$ is a hydrogen atom or a group expressed by the formula —NR$^{33}$R$^{34}$ (wherein R$^{33}$ and R$^{34}$ are defined the same as above).)

A compound 5i of the present invention, in which R$^1$ is a C$_1$ to C$_{10}$ acyl group, R$^2$ and R$^3$ separately substitute in the 6-, 7-, 8-, or 9-positions, R$^2$ is a group expressed by the formula —NR$^{37}$R$^{38}$ (wherein R$^{37}$ is a C$_1$ to C$_{10}$ alkyl group, a benzyl group, an acetyl group, or a trifluoroacetyl group, and R$^{38}$ is a hydrogen atom), and R$^3$ is a hydrogen atom or a group expressed by the formula —NR$^{37}$R$^{38}$, can be synthesized by N-alkylating and then hydrolyzing the compound 5g as shown by a reaction scheme 6-2.

Reaction Scheme 6-2

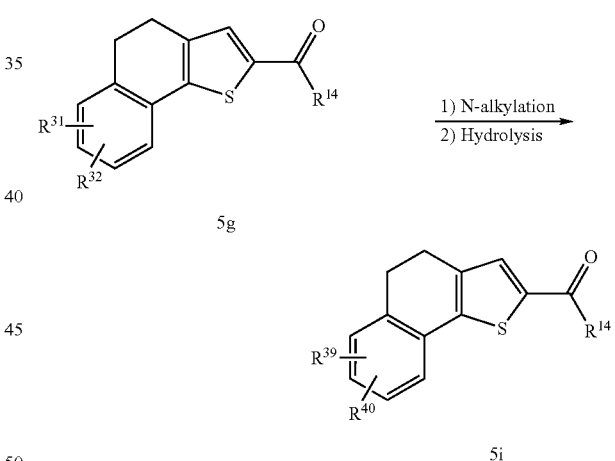

5g

5i (wherein, R$^{14}$, R$^{31}$, and R$^{32}$ are defined the same as above, R$^{39}$ is a group expressed by the formula —NR$^{37}$R$^{38}$ (wherein R$^{37}$ and R$^{38}$ are defined the same as above), and R$^{40}$ is a hydrogen atom or a group expressed by the formula —NR$^{37}$R$^{38}$ (wherein R$^{37}$ and R$^{38}$ are defined the same as above).)

A compound 5j of the present invention, in which R$^1$ is a C$_1$ to C$_{10}$ acyl group, R$^2$ and R$^3$ separately substitute in the 6-, 7-, 8-, or 9-positions, R$^2$ is a C$_1$ to C$_{10}$ alkoxy group, a C$_1$ to C$_5$ alkenyloxy group, or a C$_1$ to C$_5$ alkynyloxy group, and R$^3$ is a hydrogen atom or C$_1$ to C$_{10}$ alkoxy group, a C$_1$ to C$_5$ alkenyloxy group, or a C$_1$ to C$_5$ alkynyloxy group, can be synthesized from the compound 5b as shown by a reaction scheme 7.

Reaction Scheme 7

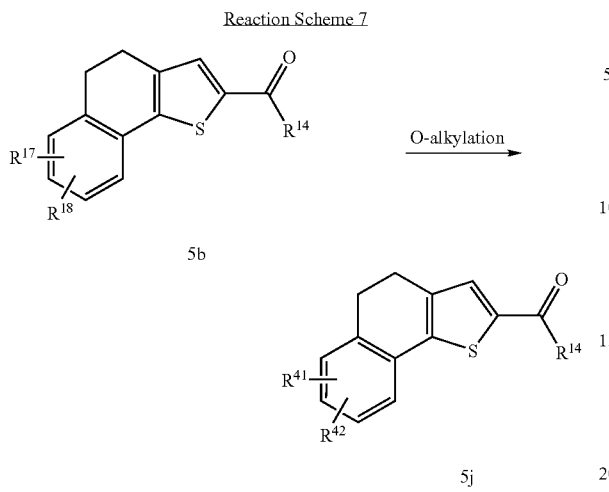

(wherein, $R^{14}$, $R^{17}$, and $R^{18}$ are defined the same as above, $R^{41}$ is a $C_1$ to $C_{10}$ alkoxy group, a $C_1$ to $C_5$ alkenyloxy group, or a $C_1$ to $C_5$ alkynyloxy group, and $R^{42}$ is a hydrogen atom, a $C_1$ to $C_{10}$ alkoxy group, a $C_1$ to $C_5$ alkenyloxy group, or a $C_1$ to $C_5$ alkynyloxy group.)

A compound 5k of the present invention, in which $R^1$ is a $C_1$ to $C_{10}$ acyl group, $R^2$ and $R^3$ separately substitute in the 6-, 7-, 8-, or 9-positions, $R^2$ is a $C_1$ to $C_{10}$ alkyl group, and $R^3$ is a hydrogen atom or a $C_1$ to $C_{10}$ alkyl group, can be synthesized by subjecting the compound 5b to triflatation and then Suzuki-Miyaura coupling as shown by a reaction scheme 8.

Reaction Scheme 8

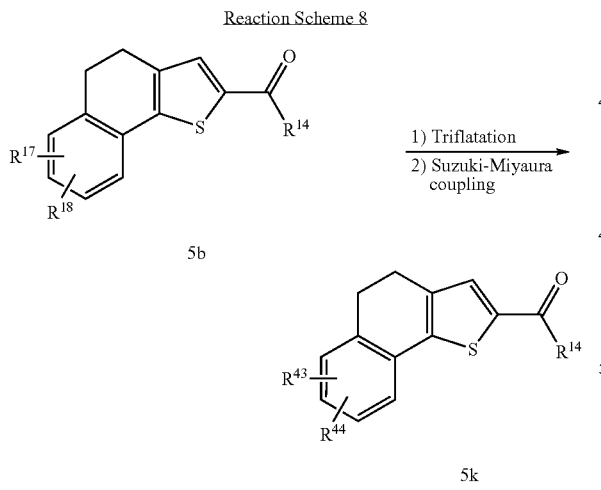

(wherein, $R^{14}$, $R^{17}$, and $R^{18}$ are defined the same as above, $R^{43}$ is a $C_1$ to $C_{10}$ alkyl group, and $R^{44}$ is a hydrogen atom or a $C_1$ to $C_{10}$ alkyl group.)

A compound 6 of the present invention, in which $R^1$ is a $C_1$ to $C_{10}$ hydroxyalkyl group, $R^2$ and $R^3$ separately substitute in the 6-, 7-, 8-, or 9-positions, $R^2$ is a halogen atom, a $C_1$ to $C_{10}$ alkyl group, a $C_1$ to $C_5$ alkenyl group, a $C_1$ to $C_5$ alkynyl group, a $C_1$ to $C_{10}$ alkoxy group, a benzyloxy group, or a group expressed by the formula —$NR^{45}R^{46}$ (wherein $R^{45}$ and $R^{46}$ are each independently a $C_1$ to $C_{10}$ alkyl group, a benzyl group, an acetyl group, or a trifluoroacetyl group), and $R^3$ is a hydrogen atom, a halogen atom, a $C_1$ to $C_{10}$ alkyl group, a $C_1$ to $C_5$ alkenyl group, a $C_1$ to $C_5$ alkynyl group, a $C_1$ to $C_{10}$ alkoxy group, a benzyloxy group, or a group expressed by the formula —$NR^{45}R^{46}$ (wherein $R^{45}$ and $R^{46}$ are each independently a $C_1$ to $C_{10}$ alkyl group, a benzyl group, an acetyl group, or a trifluoroacetyl group), or $R^2$ and $R^3$ are bonded together to form an ethylenedioxy group, can be obtained reducing a compound 51 as shown by a reaction scheme 9. The reductant used here can be sodium borohydride, lithium aluminum hydride, or the like.

Reaction Scheme 9

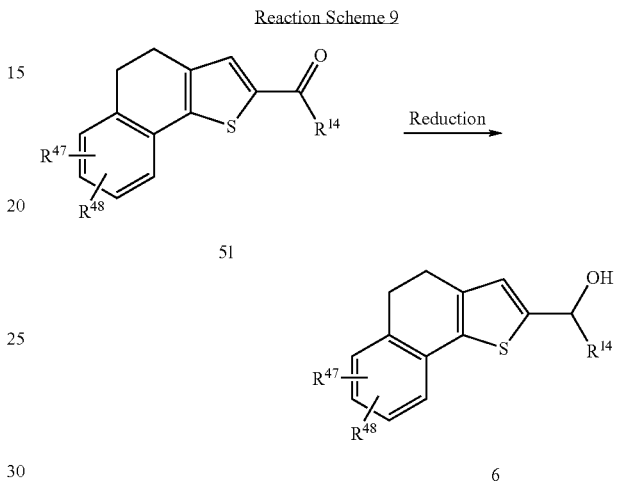

(wherein, $R^{14}$ is defined the same as above, $R^{47}$ is a halogen atom, a $C_1$ to $C_{10}$ alkyl group, a $C_1$ to $C_5$ alkenyl group, a $C_1$ to $C_5$ alkynyl group, a $C_1$ to $C_{10}$ alkoxy group, a benzyloxy group, or a group expressed by the formula —$NR^{45}R^{46}$ (wherein $R^{45}$ and $R^{46}$ are defined the same as above), and $R^{48}$ is a hydrogen atom, a halogen atom, a $C_1$ to $C_{10}$ alkyl group, a $C_1$ to $C_5$ alkenyl group, a $C_1$ to $C_5$ alkynyl group, a $C_1$ to $C_{10}$ alkoxy group, a benzyloxy group, or a group expressed by the formula —$NR^{45}R^{46}$ (wherein $R^{45}$ and $R^{46}$ are defined the same as above).)

The compound of the present invention is administered either orally or parenterally. The administered amount is from 1 to 1000 mg per dose, and this amount can be appropriately increased or decreased according to the patient's age, weight, and symptoms.

When the compound is administered orally, it is given as a formulation such as a powder, granules, capsules, or tablets, in which the compound is mixed with an excipient, binder, lubricant, antioxidant, coating agent, surfactant, plasticizer, colorant, corrective, or the like. When administered parenterally, it is given as a formulation such as an injection, or a dripping infusion. Any standard formulation method can be employed for this purpose.

The present invention will now be described in further detail by giving reference examples, examples, and test examples. In the structural formulas, BzlO indicates a benzyloxy group, and BzO a benzoyloxy group.

REFERENCE EXAMPLE 1

12 g of aluminum chloride was added under ice cooling to a mixture of 100 mL of m-xylene and 3.0 g of succinic anhydride, and this system was stirred overnight at room temperature. After the reaction, water was added under ice cooling, and the organic layer was extracted with ethyl acetate and washed with saturated brine. The product was dried with magnesium sulfate, then subjected to reduced-pressure solvent distillation to obtain 4.2 g of 4-(3,4-dimethylphenyl)-4-oxobutanoic acid in the form of a colorless solid.

6.8 mL of triethylsilane was added to a 50 mL trifluoroacetic acid solution of the 4.2 g of compound obtained above, and stirred overnight at room temperature. After the reaction, water, ethyl acetate, and a 10% sodium hydroxide aqueous solution were added under ice cooling, and stirred for 30 minutes. 1M hydrochloric acid was then added to the aqueous layer, and the precipitated crystals were filtered off to obtain 3.3 g of 4-(3,4-dimethylphenyl)butanoic acid (compound 1-1 in Table 1-1) in the form of colorless crystals.

The compounds 1-4 to 1-11 shown in Tables 1-1 and 1-2 were obtained by the same method.

REFERENCE EXAMPLE 2

18.5 mL of n-butyl lithium was added dropwise over a period of 15 minutes at −78° C. to a 30 mL tetrahydrofuran solution of 5.0 g of 2-fluoro-4-methyl-bromobenzene under nitrogen replacement. Then, a 10 mL tetrahydrofuran solution of 10.6 mL of tributyltin chloride was added dropwise over a period of 15 minutes, after which the system was stirred for 2 hours at −78° C. Upon completion of the reaction, a saturated sodium hydrogencarbonate aqueous solution was added, the system was brought to room temperature, extraction was performed with ethyl acetate, and the extract was washed with saturated brine. This product was dried with magnesium sulfate, then subjected to reduced-pressure solvent distillation, and the residue was refined by silica gel column chromatography (hexane) to obtain 9.0 g of 2-fluoro-4-methylphenyl. tributyltin in the form of a colorless oily substance.

0.5 mL of diisobutylaluminum hydride was added under nitrogen replacement to a 30 mL tetrahydrofuran solution of 0.1 g of bistriphenylphosphine palladium dichloride, and the system was stirred for 5 minutes at room temperature. A 10 mL tetrahydrofuran solution of 2.6 mL of bromomethyl crotonate and the 9.0 g of compound obtained above was added dropwise to the system, after which the system was refluxed under heating overnight. Upon completion of the reaction, the system was distilled under reduced pressure and the product was refined by silica gel column chromatography (25% ethyl acetate/hexane) to obtain methyl(2E)-4-(2-fluoro-4-methylphenyl)-2-butenoate in the form of a colorless oily substance.

1.8 g of sodium hydroxide was added to a mixed solution of the compound obtained above in 5 mL of water and 50 mL of tetrahydrofuran, and the system was refluxed under heating for 4 hours. After the reaction, reduced-pressure solvent distillation was performed, 1M hydrochloric acid was added, and the precipitated crystals were filtered off to obtain 2.8 g of (2E)-4-(2-fluoro-4-methylphenyl)-2-butenoic acid in the form of a colorless solid.

10% palladium-carbon was added to a 30 mL ethanol solution of the 2.8 g of colorless solid obtained above, and the system was stirred overnight at room temperature under hydrogen replacement. After the reaction, the system was filtered through celite, and reduced-pressure solvent distillation was performed to obtain 2.7 g of 4-(2-fluoro-4-methylphenyl)butanoic acid (compound 1-12 in Table 1-2) in the form of a colorless solid.

The compounds 1-13 and 1-14 shown in Tables 1-2 and 1-3 were obtained by the same method.

REFERENCE EXAMPLE 3

20 mL of diethyl phosphonoacetate was added under ice cooling to a 100 mL tetrahydrofuran solution 6.7 g of sodium hydride under nitrogen replacement, and this system was stirred for 30 minutes at room temperature. A 10 mL tetrahydrofuran solution of 10 g of 2-methylbenzaldehyde was added dropwise to this, and the system was refluxed under heating for 3 hours. Upon completion of the reaction, water was added under ice cooling and extraction was performed with ethyl acetate. The extracted organic layer was washed first with a saturated ammonium chloride aqueous solution, then with a saturated sodium hydrogencarbonate aqueous solution, and then with saturated brine, and dried with magnesium sulfate, after which reduced-pressure solvent distillation was performed to obtain 14.9 g of ethyl(2E)-3-(3-methylphenyl) acrylate in the form of a reddish-brown oily substance. 10% palladium-carbon was added to a 30 mL ethanol solution of the 14.9 g of compound obtained above, and the system was stirred overnight at room temperature under hydrogen replacement. After the reaction, the system was filtered through celite, and reduced-pressure solvent distillation was performed to obtain 14.0 g of ethyl-3-(3-methylphenyl) propionate in the form of a reddish-brown oily substance.

2.76 g of aluminum lithium hydride was added under nitrogen replacement and ice cooling to a 100 mL tetrahydrofuran solution of the 14.0 g of compound obtained above, and the system was brought up to room temperature and stirred for 1.5 hours. Upon completion of the reaction, a saturated ammonium chloride aqueous solution was added under ice cooling and the system was filtered through celite. Extraction was performed with ethyl acetate, the extract was washed with saturated brine and then dried with magnesium sulfate, and reduced-pressure solvent distillation was performed to obtain 10.8 g of 3-(3-methylphenyl)propan-1-ol in the form of a yellow oily substance.

12 mL of triethylamine and 6.1 mL of mesyl chloride were added under ice cooling to a 100 mL chloroform solution of the 10.8 g of compound obtained above, and the system was stirred for 2 hours at room temperature. Upon completion of the reaction, water was added under ice cooling and stirring was continued for another 30 minutes, after which the organic layer was isolated and washed first with water and then with saturated brine, dried with magnesium sulfate, and subjected to reduced-pressure solvent distillation. The residue thus obtained was dissolved in 100 mL of dimethylformamide, 4.2 g of sodium cyanide was added, and the system was stirred overnight at 100° C. Upon completion of the reaction, water was added under ice cooling, extraction was performed with ethyl acetate, and the extract was washed with saturated brine and dried with magnesium sulfate, after which reduced-pressure solvent distillation was performed to obtain 13 g of 4-(3-methylphenyl)butanenitrile in the form of a reddish-brown oily substance.

2.9 g of sodium hydroxide was added to a mixed solution of the 13 g of compound obtained above in 10 mL of water and 100 mL of ethanol, and the system was refluxed under heating overnight. Upon completion of the reaction, reduced-pressure solvent distillation was performed, 1M hydrochloric acid was added, and the precipitated crystals were filtered off to obtain 10 g of 4-(3-methylphenyl) butanoic acid (compound 1-15 in Table 1-3) in the form of a reddish-brown oily substance.

The compounds 1-16 and 1-17 shown in Table 1-3 were obtained by the same method.

TABLE 1-1

(1)

R—(3,4-positions on benzene ring)—CH₂CH₂CH₂—CO₂H with R' substituent

Structure: substituted phenyl-(CH₂)₃-CO₂H, positions 2, 3, 4 on ring, R and R'

| Compound | R | R' | Data |
|---|---|---|---|
| 1-1 | 3-Me | 4-Me | MS m/z: 191(M − H)⁻<br>¹HNMR(200 MHz, dmso-d₆) δ (ppm): 1.68-1.86(m, 2H), 2.17(s, 3H), 2.18(s, 3H), 2.49-2.51(m, 4H), 6.88 (d, J=7.9 Hz, 1H), 6.95(s, 1H), 7.03(d, J=7.9 Hz, 1H) |
| 1-4 | 3-F | 4-OMe | MS m/z: 212 (M − H)⁻<br>¹H NMR(300 MHz, dmso-d₆) δ (ppm): 1.55-1.87(m, 2H), 2.10-2.26(m, 2H), 2.37-2.64(m, 2H), 3.80(s, 3H), 6.74-7.31(m, 3H) |
| 1-5 | 4-Et | H | MS m/z: 215(M + Na)⁺<br>¹H NMR(300 MHz, dmso-d₆) δ (ppm): 1.16(t, J=7.5 Hz, 3H), 1.70-1.82(m, 2H), 2.20(t, J=7.4 Hz, 2H), 2.45-2.62(m, 4H), 7.04-7.15(m, 4H) |
| 1-6 | 4-OPr | H | MS m/z: 205(M − H)⁻<br>¹H NMR(300 MHz, dmso-d₆) δ (ppm): 0.88(t, J=7.3 Hz, 3H), 1.49-1.63(m, 2H), 1.70-1.82(m, 2H), 2.46-2.57(m, 4H), 7.02-7.14(m, 4H) |
| 1-7 | 4-OPrⁱ | H | MS m/z: 205(M − H)⁻<br>¹H NMR(300 MHz, CDCl₃) δ (ppm): 1.24(d, J=6.8 Hz, 6H), 1.89-2.01(m, 2H), 2.38(t, J=7.5 Hz, 2H), 2.64(t, J=7.5 Hz, 2H), 2.79-2.96(m, 1H), 7.07-7.17(m, 4H) |

TABLE 1-2

| Compound | R | R' | Data |
|---|---|---|---|
| 1-8 | 4-cycloHexyl | H | MS m/z: 245(M-H)⁻<br>¹H NMR(300MHz, CDCl₃) δ(ppm): 1.14-1.49(m, 5H), 1.68-1.90(m, 5H), 1.90-2.03(m, 2H), 2.38(t, J=7.5Hz, 2H), 2.42-2.54(m, 1H), 2.64(t, J=7.5Hz, 2H), 7.03-7.17(m, 4H) |
| 1-9 | 4-F | H | MS m/z: 181(M-H)⁻<br>¹HNMR(300MHz, dmso-d₆) δ(ppm): 1.65-1.88(m, 2H), 2.20(m, 2H), 2.46-2.70(m, 2H), 6.97-7.16(m, 2H), 7.17-7.30(m, 2H) |
| 1-10 | 4-Cl | H | MS m/z: 197(M-H)⁻<br>¹H NMR(200MHz, CDCl₃) δ(ppm): 1.75-2.07(m, 2H), 2.17-2.48(m, 2H), 2.53-2.71(m, 2H), 6.97-7.19(m, 2H), 7.20-7.30(m, 2H) |
| 1-11 | 3-Me | 4-OMe | MS m/z: 207(M-H)⁻<br>¹H NMR(200MHz, CDCl₃) δppm 1.83-2.02(m, 2H), 2.20(s, 3H), 2.37(t, J=7.5Hz, 2H), 2.59(t, J=7.5Hz, 2H), 3.80(s, 3H), 6.69-6.78(m, 1H), 6.91-7.02(m, 2H) |
| 1-12 | 2-F | 4-Me | MS m/z: 195(M-H)⁻<br>¹H NMR(200MHz, CDCl₃) δ(ppm): 1.80-2.03(m, 2H), 2.25-2.44(m, 5H), 2.55-2.73(m, 2H), 6.75-6.90(m, 2H), 6.96-7.11(m, 2H) |
| 1-13 | 3-F | 4-Me | MS m/z: 195(M-H)⁻<br>¹H NMR(200MHz, CDCl₃) δ(ppm): 1.77-2.02(m, 2H), 2.17-2.43(m, 5H), 2.51-2.71(m, 2H), 6.72-6.92(m, 2H), 6.96-7.18(m, 1H) |

TABLE 1-3

| Compound | R | R' | Data |
|---|---|---|---|
| 1-14 | 2-F | 4-Me | MS m/z: 211(M-H)⁻<br>¹H NMR(200MHz, CDCl₃) δ(ppm): 1.78-2.03(m, 2H), 2.37(t, J=7.4Hz, 2H), 2.64(t, J=7.3Hz, 2H), 3.77(s, 3H), 6.46-6.72(m, 2H), 6.93-7.14(m, 1H) |
| 1-15 | 3-F | H | MS m/z: 181(M-H)⁻<br>¹H NMR(200MHz, CDCl₃) δ(ppm): 1.77-2.11(m, 2H), 2.38(m, 2H), 2.56-2.79(m, 2H), 6.78-7.03(m, 3H), 7.13-7.34(m, 1H) |
| 1-16 | 3-Cl | H | MS m/z: 197(M-H)⁻<br>¹H NMR(200MHz, CDCl₃) δ(ppm): 1.86-2.07(m, 2H), 2.26-2.46(m, 2H), 2.58-2.74(m, 2H), 7.11-7.37(m, 4H) |
| 1-17 | 3-Me | H | MS m/z: 177(M-H)⁻<br>¹H NMR(200MHz, CDCl₃) δ(ppm): 1.84-2.06(m, 2H), 2.28-2.46(m, 5H), 2.54-2.74(m, 2H), 6.86-7.32(m, 4H) |

REFERENCE EXAMPLE 4

2.5 mL of thionyl chloride was added at room temperature to a 60 mL chloroform solution of 3.3 g of compound 1-1 obtained in Reference Example 1, and the system was refluxed under heating, for 10 hours. After the reaction, reduced-pressure solvent distillation was performed to obtain 4-(3,4-dimethylphenyl)butanoyl chloride.

4.5 g of aluminum chloride was added under ice cooling to a 100 mL chloroform solution of the compound obtained above, and the system was stirred for 2 hours at room temperature. After the reaction, water was added under ice cooling, extraction was performed with ethyl acetate, and the organic layer was washed with saturated brine, dried with magnesium sulfate, and then subjected to reduced-pressure solvent distillation, and the residue was refined by silica gel column chromatography (10% ethyl acetate/hexane) to obtain 1.7 g of 6,7-dimethyltetralone (compound 2-2 in Table 2-1) in the form of a colorless solid.

The compounds 2-3, 2-9, and 2-11 to 2-23 shown in Tables 2-1 to 2-4 were obtained by the same method.

TABLE 2-1

(2)

| Compound | R | R' | Data |
|---|---|---|---|
| 2-2 | 6-Me | 7-Me | MS m/z: 175(M + H)$^+$<br>$^1$H NMR(200 MHz, CDCl$_3$) δ (ppm): 2.14-2.17(m, 2H), 2.26(s, 3H), 2.30(s, 3H), 2.62(t, J=6.4 Hz, 2H), 2.90(t, J=6.4 Hz, 2H), 7.03(s, 1H), 7.81(s, 1H) |
| 2-3 | 7-Me | H | MS m/z: 183(M + Na)$^+$<br>$^1$H NMR(200 MHz, CDCl$_3$) δ ppm): 2.05-2.18(m, 2H), 2.36(s, 3H), 2.64(t, J=6.3 Hz, 2H), 2.91(t, J=6.3 Hz, 2H), 7.14(d, J=7.9 Hz, 1H), 7.29(d, J=7.9 Hz, 1H), 7.85(s, 1H) |

TABLE 2-1-continued (2)

| Compound | R | R' | Data |
|---|---|---|---|
| 2-9 | 6,7-Ethylenedioxy | | MS m/z: 227(M + Na)$^+$<br>$^1$H NMR(200 MHz, CDCl$_3$) δ (ppm): 2.02-2.15(m, 2H), 2.58(t, J=5.9 Hz, 2H), 2.84(t, J=5.9 Hz, 2H), 4.20-4.38(m, 4H), 6.71(s, 1H), 7.56(s, 1H) |
| 2-10 | 7-F | H | MS m/z: 165(M + H)$^+$<br>$^1$H NMR(200 MHz, CDCl$_3$) δ (ppm): 2.06-2.23(m, 2H), 2.55-2.72(m, 2H), 2.84-3.00(m, 2H), 7.03-7.31(m, 2H), 7.68(dd, J=9.3, 2.6 Hz, 1H) |
| 2-11 | 6-F | 7-OMe | MS m/z: 195(M + H)$^+$<br>$^1$H NMR(200 MHz, CDCl$_3$) δ (ppm): 2.05-2.20(m, 2H), 2.50-2.68(m, 2H), 2.80-2.96(m, 2H), 6.95(d, J=11.4 Hz, 1H), 7.62(d, J=9.0 Hz, 1H) |

TABLE 2-2

| Compound | R | R' | Data |
|---|---|---|---|
| 2-12 | 7-Et | H | MS m/z: 197(M+Na)$^+$<br>$^1$H NMR(200MHz, CDCl$_3$) δ(ppm): 1.24(t, J=7.5Hz, 3H), 2.04-2.20(m, 2H), 2.58-2.75(m, 4H), 2.93(t, J=6.2Hz, 2H), 7.17(d, J=8.0Hz, 1H), 7.32(dd, J=8.0Hz, J=1.8Hz, 1H), 7.83-7.93(m, J=1.8Hz, 1H) |
| 2-13 | 7-Pr | H | MS m/z: 211(M+Na)$^+$<br>$^1$H NMR(300MHz, CDCl$_3$) δ(ppm): 0.93(t, J=7.3Hz, 3H), 1.57-1.72(m, 2H), 2.07-2.18(m, 2H), 2.56-2.68(m, 4H), 2.93(t, J=6.1Hz, 2H), 7.17(d, J=7.8Hz, 1H), 7.30(dd, J=7.8, 2.0Hz, 1H), 7.85(d, J=2.0Hz, 1H) |
| 2-14 | 7-Pr$^i$ | H | MS m/z: 211(M+Na)$^+$<br>$^1$H NMR(300MHz, CDCl$_3$) δ(ppm): 1.25(d, J=6.8Hz, 6H), 2.05-2.20(m, 21H), 2.58-2.69(m, 2H), 2.87-2.99(m, 3H), 7.19(d, J=7.9Hz, 1H), 7.35(dd, J=7.9, 2.0Hz, 1H), 7.91(d, J=2.0Hz, 1H) |
| 2-15 | 7-cycloHexyl | H | MS m/z: 251(M+Na)$^+$<br>$^1$H NMR(300MHz, CDCl$_3$) δ(ppm): 1.16-1.51(m, 5H), 1.68-1.91(m, 5H), 2.06-2.20(m, 2H), 2.43-2.58(m, 1H), 2.60-2.69(m, 2H), 2.89-2.97(m, 2H), 7.18(d, J=7.8Hz, 1H), 7.33(dd, J=7.8, 2.0Hz, 1H), 7.89(d, J=2.0Hz, 1H) |

TABLE 2-3

| Compound | R | R' | Data |
|---|---|---|---|
| 2-16 | 7-Cl | H | MS m/z: 181(M+H)$^+$<br>$^1$H NMR(200MHz, CDCl$_3$) δ(ppm): 2.04-2.23(m, 2H), 2.57-2.72(m, 2H), 2.86-3.01(m, 2H), 7.19(d, J=8.4Hz, 1H), 7.42(dd, J=8.4, 2.2Hz, 1H), 7.99(d, J=2.2Hz, 1H) |
| 2-17 | 6-Me | 7-OMe | MS m/z: 191(M+H)$^+$<br>$^1$H NMR(300MHz, CDCl$_3$) δ(ppm): |

TABLE 2-3-continued

| Compound | R | R' | Data |
|---|---|---|---|
|  |  |  | 2.04-2.16(m, 2H), 2.25(s, 3H), 2.57-2.66(m, 2H), 2.86(t, J=6.1Hz, 2H), 3.86(s, 3H), 7.02(s, 1H), 7.45(s, 1H) |
| 2-18 | 5-F | 7-Me | MS m/z: 179(M+H)$^+$<br>$^1$H NMR(200MHz, CDCl$_3$) δ(ppm): 2.05-2.22(m, 4H), 2.36(s, 3H), 2.56-2.74(m, 2H), 2.83-2.95(m, 2H), 7.05(d, J=9.7Hz, 1H), 7.65(s, 1H) |
| 2-19 | 6-F | 7-Me | MS m/z: 179(M+H)$^+$<br>$^1$H NMR(200MHz, CDCl$_3$) δ(ppm): 2.07-2.45(m, 5H), 2.47-2.75(m, 2H), 2.78-2.99(m, 2H), 6.87(d, J=9.7Hz, 1H), 7.90(d, J=8.4Hz, 1H) |
| 2-20 | 5-F | 7-OMe | MS m/z: 195(M+H)$^+$<br>$^1$H NMR(200MHz, CDCl$_3$) δ(ppm): 1.93-2.20(m, 2H), 2.49-2.75(m, 2H), 2.77-3.03(m, 2H), 3.83(s, 3H), 6.83(dd, J=10.6, 2.4Hz, 1H), 7.35(d, J=2.4Hz, 1H) |
| 2-21 | 6-F | H | MS m/z: 187(M+Na)$^+$<br>$^1$H NMR(200MHz, CDCl$_3$) δ(ppm): 1.89-2.27(m, 2H), 2.48-2.73(m, 2H), 2.81-3.05(m, 2H), 6.74-7.09(m, 2H), 8.06(dd, J=8.6, 5.9Hz, 1H) |

TABLE 2-4

| Compound | R | R' | Data |
|---|---|---|---|
| 2-22 | 6-Cl | H | MS m/z: 181(M+H)$^+$<br>$^1$H NMR(200MHz, CDCl$_3$) δ(ppm): 1.99-2.29(m, 2H), 2.53-2.76(m, 2H), 2.87-3.10(m, 2H), 7.13-7.37(m, 1H), 7.38-7.59(m, 1H), 7.88-8.12(m, 1H) |
| 2-23 | 6-Me | H | MS m/z: 161(M+H)$^+$<br>$^1$H NMR(200MHz, CDCl$_3$) δ(ppm): 1.98-2.23(m, 2H), 2.37(s, 3H), 2.47-2.76(m, 2H), 2.75-3.03(m, 2H), 7.06(s, 1H), 7.11(d, J=7.9Hz, 1H), 7.93(d, J=7.9Hz, 1H) |

REFERENCE EXAMPLE 5

3.1 g of t-butoxypotassium was added under ice cooling and nitrogen replacement to a 50 mL dimethylformamide solution of 4.0 g of 5-hydroxytetralone, and the system was stirred for 15 minutes at the same temperature, after which 3.2 mL of benzyl bromide was added, and the system was stirred for 2 hours at the same temperature. After the reaction, water was added, extraction was performed with ethyl acetate, and the organic layer was washed with saturated brine and dried with magnesium sulfate, then subjected to reduced-pressure solvent distillation, and the residue was refined by silica gel column chromatography (20% ethyl acetate/hexane) to obtain 6.3 g of 5-benzyloxytetralone (compound 2-7 in Table 3-1) in the form of a colorless solid.

The compounds 2-8 and 2-24 to 2-28 shown in Tables 3-1 and 3-2 were obtained by the same method.

TABLE 3-1

(2)

| Compound | R | R' | Data |
|---|---|---|---|
| 2-7 | 5-OBzl | H | MS m/z: 253(M + H)$^+$<br>$^1$H NMR(300 MHz, CDCl$_3$) δ (ppm): 2.04-2.18(m, 2H), 2.64(t, J=6.0 Hz, 2H), 2.99(t, J=6.0 Hz, 2H), 5.11(s, 2H), 7.09(d, J=7.9 Hz, 1H), 7.25(t, J=7.9 Hz, 1H), 7.32-7.51(m, 5H), 7.67(d, J=7.9 Hz, 1H) |
| 2-8 | 6-OBzl | H | MS m/z: 275(M + Na)$^+$<br>$^1$H NMR(300 MHz, CDCl$_3$) δ (ppm): 2.08-2.18(m, 2H), 2.61(t, J=6.1 Hz, 2H), 2.92(t, J=6.1 Hz, 2H), 5.12(s, 2H), 6.79(d, J=2.5 Hz, 1H), 6.90(dd, J=8.7, 2.5 Hz, 1H), 7.29-7.48(m, 5H), 8.01(d, J=8.7 Hz, 1H) |
| 2-24 | 6-OEt | H | MS m/z: 213(M + Na)$^+$<br>$^1$H NMR(300 MHz, CDCl$_3$) δ (ppm): 1.43(t, J=7.0 Hz, 3H), 2.06-2.16(m, 2H), 2.57-2.63(m, 2H), 2.92(t, J=6.1 Hz, 2H), 4.09(q, J=7.0 Hz, 2H), 6.69(d, J=2.5 Hz, 1H), 6.81(dd, J=8.7, 2.5 Hz, 1H), 8.00(d, J=8.7 Hz, 1H) |
| 2-25 | 6-O-cyclo-Hexyl-methyl | H | MS m/z: 281(M + Na)$^+$<br>$^1$H NMR(300 MHz, CDCl$_3$) δ (ppm): 0.96-1.40(m, 5H), 1.65-1.91(m, 6H), 2.06-2.16(m, 2H), 2.55-2.64(m, 2H), 2.92(t, J=6.0 Hz, 2H), 3.80(d, J=6.2 Hz, 2H), 6.69(d, J=2.5 Hz, 1H), 6.81(dd, J=8.7, 2.5 Hz, 1H), 8.00(d, J=8.7 Hz, 1H) |

TABLE 3-2

| Compound | R | R' | Data |
|---|---|---|---|
| 2-26 | 6-OPr | H | MS m/z: 227(M+Na)+<br>$^1$H NMR(300MHz, CDCl$_3$) δ(ppm):<br>1.04(t, J=7.5Hz, 3H), 1.75-1.89(m, 2H),<br>2.06-2.18(m, 2H), 2.56-2.66(m, 2H),<br>2.91(t, J=6.1Hz, 2H), 3.97(t, J=6.6Hz, 2H),<br>6.70(d, J=2.5Hz, 1H), 6.81(dd,<br>J=8.8, 2.5Hz, 1H), 8.00(d, J=8.8Hz, 1H) |
| 2-27 | 6-OPr$^i$ | H | MS m/z: 227(M+Na)+<br>$^1$H NMR(200MHz, CDCl$_3$) δ(ppm):<br>1.36(d, J=6.2Hz, 6H), 2.04-2.21(m, 2H),<br>2.52-2.67(m, 2H), 2.91(t, J=6.2Hz, 2H),<br>4.51-4.75(m, 1H), 6.67(d, J=2.6Hz, 1H),<br>6.79(dd, J=8.6, 2.6Hz, 1H), 7.99(d,<br>J=8.6Hz, 1H) |
| 2-28 | 6-OBz | H | MS m/z: 289(M+Na)+<br>$^1$H NMR(300MHz, CDCl$_3$) δ(ppm):<br>2.11-2.23(m, 2H), 2.64-2.71(m, 2H),<br>3.01(t, J=6.1Hz, 2H), 7.13-7.19(m, 2H),<br>7.49-7.57(m, 2H), 7.62-7.74(m, 1H),<br>8.10-8.23(m, 3H) |

REFERENCE EXAMPLE 6

12.4 g of potassium hydroxide was added to a mixed solution of 9.0 g of 6-acetamidetetralone in 80 mL of methanol and 20 mL of water, and the system was refluxed under heating for 9 hours. After the reaction, reduced-pressure solvent distillation was performed, water was added, and extraction was performed with ethyl acetate. The extracted organic layer was washed with saturated brine and dried with magnesium sulfate, then subjected to reduced-pressure solvent distillation to obtain 6.5 g of 6-aminotetralone in the form of a dark brown solid.

6.8 mL of trifluoroacetic anhydride and 8.4 mL of triethylamine were added under ice cooling to 6.5 g of the compound obtained above in a 70 mL tetrahydrofuran solution, and the system was stirred for 4 hours under ice cooling. After the reaction, water was added under ice cooling, and extraction was performed with ethyl acetate. The extracted organic layer was washed with saturated brine and dried with magnesium sulfate, then subjected to reduced-pressure solvent distillation to obtain 10 g of 6-trifluoroacetamidetetralone (compound 2-29) in the form of a dark brown solid.

Compound 2-29

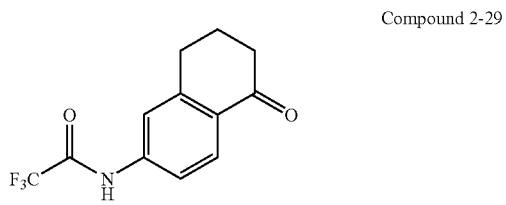

MS m/z: 256 (M–H)−

$^1$H NMR (200 MHz, CDCl$_3$) δ (ppm):2.06-2.12 (m, 2H), 2.67 (t, J=6.2 Hz, 2H), 2.99 (t, J=6.2 Hz, 2H) 7.37 (dd, J=8.4, 2.0 Hz, 1H), 7.70 (d, J=2.0 Hz, 1H), 8.07 (d, J=8.4 Hz, 1H)

REFERENCE EXAMPLE 7

3.5 mL of phosphorus oxychloride was added dropwise to 4.5 mL of dimethylformamide under ice cooling, after which the system was brought up to room temperature and stirred for 30 minutes. To this was added a solution of 5.0 g of 5,7-dimethyltetralone in 100 mL of chloroform, and the system was refluxed under heating overnight. After the reaction, water was added and the system was stirred for 30 minutes, after which the organic layer was washed first with a saturated sodium hydrogencarbonate aqueous solution and then with saturated brine, dried with magnesium sulfate, and then subjected to reduced-pressure solvent distillation, and the residue was refined by silica gel column chromatography (5% ethyl acetate/hexane) to obtain 5.8 g of 1-chloro-2-formyl-3,4-dihydronaphthalene in the form of a dark brown solid.

3.2 mL of ethyl thioglycolate and 8.3 g of potassium carbonate were added to a solution of the 5.8 g of compound obtained above in 50 mL of acetonitrile, and the system was stirred overnight at room temperature. After the reaction, ethyl acetate was added, and the organic layer was washed first with water, then with a 10% sodium hydroxide aqueous solution, and then with saturated brine, dried with magnesium sulfate, and then subjected to reduced-pressure solvent distillation, and the residue was refined by silica gel column chromatography (2.5% ethyl acetate/hexane) to obtain 4.9 g of ethyl 4,5-dihydro-6,8-dimethylnaphtho[1,2-b]thiophene-2-carboxylate (compound 3-1 in Table 4-1) in the form of a dark brown solid.

The compounds 3-2 to 3-11 and 3-25 shown in Tables 4-1 to 4-3 were obtained by the same method.

TABLE 4-1

(3)

| Compound | R | R' | Data |
|---|---|---|---|
| 3-1 | 6-Me | 8-Me | MS m/z: 309(M + Na)+<br>$^1$H NMR(200 MHz, CDCl$_3$) δ (ppm):<br>1.38 (t, J=7.1 Hz, 3H), 2.30(s, 3H),<br>2.32(s, 3H), 2.69-3.01(m, 4H), 4.35(q,<br>J=7.1 Hz, 2H), 6.94(s, 1H), 7.14(s, 1H),<br>7.59(s, 1H) |
| 3-2 | 7-Me | 8-Me | MS m/z: 309(M + Na)+<br>$^1$H NMR(200 MHz, CDCl$_3$) δ (ppm):<br>1.38(t, J=7.0 Hz, 3H), 2.26(s, 6H),<br>2.65-2.98 (m, 4H), 4.35(q, J=7.0 Hz, 2H),<br>7.01(s, 1H), 7.22(s, 1H), 7.59 (s, 1H) |
| 3-3 | 8-Me | H | MS m/z: 295(M + Na)+<br>$^1$H NMR(200 MHz, CDCl$_3$) δ (ppm):<br>1.39(t, J=7.3 Hz, 3H), 2.36(s, 3H),<br>2.73-3.00(m, 4H), 4.38(q, J=7.3 Hz, 2H),<br>7.04(d, J=7.3 Hz, 1H), 7.13(d, J=7.3 Hz,<br>1H), 7.26(s, 1H), 7.61(s, 1H) |
| 3-4 | 6-OMe | H | MS m/z: 311(M + Na)+<br>$^1$H NMR(200 MHz, CDCl$_3$) δ (ppm):<br>1.39 (t, J=7.0 Hz, 3H), 2.69-3.08(m, 4H),<br>3.89(s, 3H), 4.36(q, J=7.0 Hz, 2H),<br>6.83(d, J=7.7 Hz, 1H), 7.08(d, J=7.7 Hz,<br>1H), 7.21(t, J=7.7 Hz, 1H), 7.60(s, 1H) |
| 3-5 | 7-OMe | H | MS m/z: 311(M + Na)+<br>$^1$H NMR(200 MHz, CDCl$_3$) δ (ppm):<br>1.39(t, J=7.0 Hz, 3H), 2.73-3.03(m, 4H),<br>3.84(s, 3H), 4.37(q, J=7.0 Hz, 2H),<br>6.75-6.81(m, 2H), 7.37(d, J=9.2 Hz, 1H,<br>7.58(s, 1H) |

TABLE 4-2

| Compound | R | R' | Data |
|---|---|---|---|
| 3-6 | 8-OMe | H | MS m/z: 311(M+Na)+ <br> $^1$H NMR(200MHz, CDCl$_3$) δ(ppm): 1.40(t, J=7.2Hz, 3H), 2.68-3.05(m, 4H), 3.84(s, 3H), 4.37(q, J=7.2Hz, 2H), 6.77(dd, J=2.4, 8.1Hz, 1H), 6.98(d, J=2.4Hz, 1H), 7.16(d, J=8.1Hz, 1H), 7.60(s, 1H) |
| 3-7 | 6-OBzl | H | MS m/z: 365(M+H)+ <br> $^1$H NMR(200MHz, CDCl$_3$) δppm): 1.38(t, J=7.1Hz, 3H), 2.76-2.98(m, 4H), 4.35(q, J=7.1Hz, 2H), 5.09(s, 2H), 6.81(d, J=2.6Hz, 1H), 6.88(s, 1H), 7.30-7.46(m, 6H), 7.60(s, 1H) |
| 3-8 | 7-OBzl | H | MS m/z: 365(M+H)+ <br> $^1$H NMR(200MHz, CDCl$_3$) δ(ppm): 1.40(t, J=7.0Hz, 3H), 2.81(t, J=7.7Hz, 2H), 3.06(t, J=7.7Hz, 2H), 4.37(q, J=7.0Hz, 2H), 5.11(s, 2H), 6.90(d, J=7.3Hz, 1H), 7.10(d, J=7.3Hz, 1H), 7.17(t, J=7.3Hz, 1H), 7.34-7.49(m, 5H), 7.60(s, 1H) |
| 3-9 | 6,7-Ethylenedioxy | | MS m/z: 339(M+Na)+ <br> $^1$H NMR(200MHz, CDCl$_3$) δ(ppm): 1.38(t, J=7.1Hz, 3H), 2.72-2.90(m, 4H), 4.27(s, 4H), 4.37(q, J=7.1Hz, 2H), 6.74(s, 1H), 6.96(s, 1H), 7.57(s, 1H) |
| 3-10 | 8-F | H | MS m/z: 277(M+H)+ <br> $^1$H NMR(200MHz, CDCl$_3$) δ(ppm): 1.39(t, J=7.0Hz, 3H), 2.69-3.02(m, 4H), 4.36(q, J=7.0Hz, 2H), 6.78-6.96(m, 1H), 7.05-7.23(m, 2H), 7.60(s, 1H) |

TABLE 4-3

| Compound | R | R' | Data |
|---|---|---|---|
| 3-11 | 7-F | 8-OMe | MS m/z: 307(M+H)+ <br> $^1$H NMR(200MHz, CDCl$_3$) δppm): 1.39(t, J=7.3Hz, 3H), 2.73-2.94(m, 4H), 3.92(s, 3H), 4.36(q, J=7.3Hz, 2H), 6.96(d, J=11.4Hz, 1H), 6.99(d, J=7.9Hz, 1H), 7.59(s, 1H) |
| 3-25 | 8-NO$_2$ | H | $^1$H NMR(200MHz, CDCl$_3$) δ(ppm): 1.41(t, J=8.2Hz, 3H), 2.83-2.98(m, 2H), 3.01-3.13(m, 2H), 4.38(q, J=8.2Hz, 2H), 7.40(d, J=8.0Hz, 1H), 7.63(s, 1H), 8.07(dd, J=2.5, 8.0Hz, 1H), 8.24(d, J=2.5Hz, 1H) |

REFERENCE EXAMPLE 8

11 g of iron and 1.3 g of ammonium chloride were added to a mixed solution of 12 g of the compound obtained in Reference Example 7 (3-25) in 120 mL of ethanol and 12 mL of water, and the system was refluxed under heating for 2 hours. After the reaction, the insolubles were filtered off, and the crystals that precipitated in the filtrate were filtered off to obtain 7.1 g of ethyl 8-amino-4,5-dihydronaphtho[1,2-b]thiophene-2-carboxylate (compound 3-26) in the form of colorless crystals.

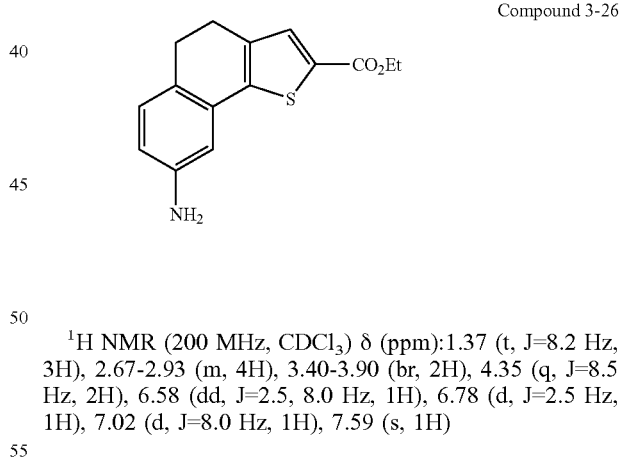

Compound 3-26

$^1$H NMR (200 MHz, CDCl$_3$) δ (ppm):1.37 (t, J=8.2 Hz, 3H), 2.67-2.93 (m, 4H), 3.40-3.90 (br, 2H), 4.35 (q, J=8.5 Hz, 2H), 6.58 (dd, J=2.5, 8.0 Hz, 1H), 6.78 (d, J=2.5 Hz, 1H), 7.02 (d, J=8.0 Hz, 1H), 7.59 (s, 1H)

REFERENCE EXAMPLE 9

0.82 g of sodium hydroxide was added to a mixed solution of 4.9 g of the compound obtained in Reference Example 7 (3-1) in 100 mL of ethanol and 10 mL of water, and the system was stirred overnight at 80° C. After the reaction, reduced-pressure solvent distillation was performed, 1M hydrochloric acid was added, and the precipitated crystals were filtered off to obtain 4.4 g of 4,5-dihydro-6,8-dimethylnaphtho[1,2-b]thiophene-2-carboxylic acid in the form of colorless crystals.

4.2 g of 1-ethyl-3-(3-dimethylaminopropyl)carbodiimide hydrochloride was added to a 100 mL dimethylformamide solution of the compound obtained above, 2.0 g of N,O-dimethylhydroxylamine hydrochloride, 3.0 g of 1-hydroxybenzotriazole, and 3.1 mL of triethylamine, and the system was stirred for 5 hours at room temperature. After the reaction, ethyl acetate was added, and the extract was washed first with a saturated sodium hydrogencarbonate aqueous solution and then with saturated brine, dried with magnesium sulfate, and then subjected to reduced-pressure solvent distillation, and the residue was refined by silica gel column chromatography (25% ethyl acetate/hexane) to obtain 4.7 g of 4,5-dihydro-6,8-dimethylnaphtho[1,2-b]thiophene-2-N,O-dimethylhydroxylcarboxamide (compound 4-1 in Table 5-1) in the form of a dark brown solid.

The compounds 4-2 to 4-12 shown in Tables 5-1 to 5-3 were obtained by the same method.

TABLE 5-1

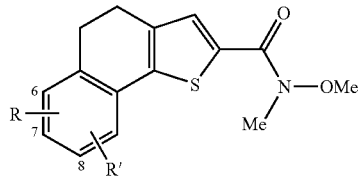

(4)

| Compound | R | R' | Data |
|---|---|---|---|
| 4-1 | 6-Me | 8-Me | MS m/z: 302(M + H)+ <br> $^1$HNMR(300 MHz, CDCl$_3$) δ (ppm): 2.30(s, 3H), 2.31(s, 3H), 2.70-2.96(m, 4H), 3.38(s, 3H), 3.83(s, 3H), 6.93(s, 1H), 7.16(s, 1H), 7.75(s, 1H) |
| 4-2 | 7-Me | 8-Me | MS m/z: 302(M + H)+ <br> $^1$HNMR(200 MHz, CDCl$_3$) δ (ppm): 2.26(s, 3H), 2.27(s, 3H), 2.68-3.09(m, 4H), 3.39(s, 3H), 3.84(s, 3H), 7.02(s, 1H), 7.26(s, 1H), 7.76(s, 1H) |
| 4-3 | 8-Me | H | MS m/z: 310(M + H)+ <br> $^1$H NMR(200 MHz, CDCl$_3$) δ (ppm): 2.36(s, 3H), 2.75-3.01(m, 4H), 3.39(s, 3H), 3.83(s, 3H), 7.02(d, J=7.9 Hz, 1H), 7.13(d, J=7.9 Hz, 1H), 7.30(s, 1H), 7.76(s, 1H) |
| 4-4 | 6-OMe | H | MS m/z: 304(M + H)+ <br> $^1$H NMR(200 MHz, CDCl$_3$) δ (ppm): 2.68-3.11(m, 4H), 3.39(s, 3H), 3.80(s, 3H), 3.88(s, 3H), 6.82(d, J=7.0 Hz, 1H), 7.11(d, J=7.0 Hz, 1H), 7.18(t, J=7.0 Hz, 1H), 7.77(s, 1H) |
| 4-5 | 7-OMe | H | MS m/z: 304(M + H)+ <br> $^1$H NMR(200 MHz, CDCl$_3$) δ (ppm): 2.77-2.99(m, 4H), 3.40(s, 3H), 3.81(s, 3H), 3.84(s, 3H), 6.73 (d,J=2.6 Hz, 1H), 6.81(s, 1H), 7.38(d, J=2.6 Hz, 1H), 7.76(s, 1H) |

TABLE 5-2

| Compound | R | R' | Data |
|---|---|---|---|
| 4-6 | 8-OMe | H | MS m/z: 304(M+H)+ <br> $^1$H NMR(200MHz, CDCl$_3$) δ(ppm): 2.71-2.95(m, 4H), 3.40(s, 3H), 3.83(s, 3H), 3.85(s, 3H), 6.77(dd, J=2.6, 8.4Hz, 1H), 7.01(d, J=2.6Hz, 1H), 7.14(d, J=8.4Hz, 1H), 7.76(s, 1H) |
| 4-7 | 6-OBzl | H | MS m/z: 402(M+Na)+ <br> $^1$H NMR(200MHz, CDCl$_3$3) δ(ppm): 2.71-3.15(m, 4H), 3.38(s, 3H), 3.83(s, 3H), 5.11(s, 2H), 6.89(dd, J=1.8, 7.5Hz, 1H), 7.06-7.49(m, 7H), 7.77(s, 1H) |
| 4-8 | 7-OBzl | H | MS m/z: 402(M+Na)+ <br> $^1$H NMR(200MHz, CDCl$_3$) δ(ppm): 2.77-2.98(m, 4H), 3.38(s, 3H), 3.82(s, 3H), 5.10(s, 2H), 6.82(d, J=2.6Hz, 1H), 6.88(s, 1H), 7.33-7.48(m, 6H), 7.75(s, 1H) |
| 4-9 | 6,7-Ethylenedioxy | | MS m/z: 354(M+Na)+ <br> $^1$H NMR(200MHz, CDCl$_3$) δ(ppm): 2.72-2.91(m, 4H), 3.38(s, 3H), 3.80(s, 3H), 4.26(s, 4H), 6.74(s, 1H), 6.99(s, 1H), 7.73(s, 1H) |
| 4-10 | 8-F | H | MS m/z: 314(M+Na)+ <br> $^1$H NMR(200MHz, CDCl$_3$) δ(ppm): 2.58-3.01(m, 4H), 3.39(s, 3H), 3.82(s, 3H), 6.75-6.98(m, 1H), 7.05-7.24(m, 2H), 7.77(s, 1H) |
| 4-11 | 7-F | 8-OMe | MS n/z: 344(M+Na)+ <br> $^1$H NMR(200MHz, CDCl$_3$) δ(ppm): 2.64-3.04(m, 4H), 3.39(s, 3H), 3.83(s, 3H), 3.94(s, 3H), 6.84-7.11(m, 2H), 7.75(s, 1H) |

TABLE 5-3

| Compound | R | R' | Data |
|---|---|---|---|
| 4-12 | 8-NH$_2$ | H | $^1$H NMR(200MHz, CDCl$_3$) δ(ppm): 2.68-2.93(m, 4H), 3.37(s, 3H), 3.80(s, 3H), 4.53(brs, 2H), 6.56(dd, J=2.5, 8.0Hz, 1H), 6.81(d, J=2.5Hz, 1H), 7.02(d, J=8.0Hz, 1H), 7.72(s, 1H) |

REFERENCE EXAMPLE 10

1.1 mL of methyl iodide and 0.46 g of sodium hydrogencarbonate were added to a 10 mL dimethylformamide solution of 0.52 g of the compound obtained in Reference Example 9 (4-12), and the system was stirred overnight at room temperature, and then stirred for another 6 hours in a 100° C. oil bath. After the reaction, ethyl acetate was added, the organic layer was washed first with water and then with saturated brine, dried with magnesium sulfate, and then subjected to reduced-pressure solvent distillation to obtain 0.36 g of 4,5-dihydro-8-(dimethylamino)naphtho [1,2-b]thiophene-2-N,O-dimethylhydroxylcarboxamide (compound 4-13) in the form of a dark brown oily substance.

Compound 4-13

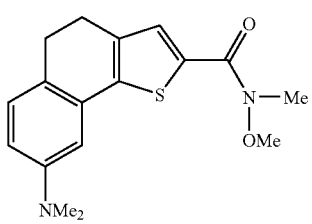

$^1$H NMR (200 MHz, CDCl$_3$) δ (ppm):2.73-2.90 (m, 4H), 2.98(s, 6H), 3.39 (s, 3H), 383 (s, 3H), 6.64 (dd, J=2.5, 8.0 Hz, 1H), 6.83 (d, J=2.5 Hz, 1H), 7.11 (d, J=8.0 Hz, 1H), 7.76 (s, 1H)

Compounds 4-14 and 4-15 were obtained by the same method.

Compound 4-14

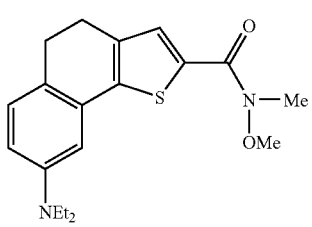

$^1$H NMR (200 MHz, CDCl$_3$) δ (ppm): 1.14(t, J=8.5 Hz, 6H), 2.72-2.92 (m, 4H), 3.36 (q, J=8.5 Hz, 4H), 3.38 (s, 3H), 3.83 (s, 3H), 6.58 (dd, J=2.5, 8.0 Hz, 1H), 6.89 (d, J=2.5 Hz, 1H), 7.08 (d, J=8.0 Hz, 1H), 7.74 (s, 1H)

Compound 4-15

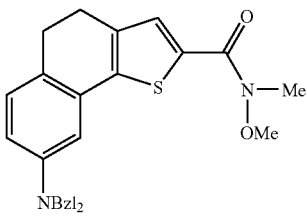

$^1$H NMR (200 MHz, CDCl$_3$) δ (ppm):2.77-2.92 (m, 4H), 3.36 (s, 3H), 3.76 (s, 3H), 4.66 (s, 4H), 6.62 (dd, J=2.5, 8.0 Hz, 1H), 6.88 (d, J=2.5 Hz, 1H), 7.02 (d, J=8.0 Hz, 1H), 7.15-7.42 (m, 10H), 7.72 (s, 1H)

REFERENCE EXAMPLE 11

First 1.1 mL of triethylamine and then 1.1 mL of trifluoroacetic anhydride were added under ice cooling to a 10 mL tetrahydrofuran solution of 1.8 g of the compound obtained in Reference Example 9 (compound 4-12), and the system was stirred for 2 hours at the same temperature. After the reaction, ice was added, extraction was performed with ethyl acetate, and the extract was washed with saturated brine, dried with magnesium sulfate, and then subjected to reduced-pressure solvent distillation. The residue was washed with ethyl acetate to obtain 1.3 g of 4,5-dihydro-8-(trifluoroacetylamino)naphtho[1,2-b]thiophene-2-N,O-dimethylhydroxylcarboxamide in the form of light brown crystals.

Next, 0.15 g of 60% oily sodium hydride was washed with hexane, after which 5 mL of dimethylformamide was added. An 8 mL dimethylformamide solution of 1.3 g of the compound obtained in the pre-reaction was added under ice cooling, and the system was stirred for 20 minutes at the same temperature. 0.28 mL of methyl iodide was added under ice cooling, and the system was stirred overnight at room temperature. After the reaction, water was added, extraction was performed with ethyl acetate, and the organic layer was washed with saturated brine, dried with magnesium sulfate, and subjected to reduced-pressure solvent distillation. The residue was refined by silica gel column chromatography (30% ethyl acetate/hexane) to obtain 1.3 g of 4,5-dihydro-8-(trifluoroacetylamino)naphtho[1,2-b]thiophene-2-N,O-dimethylhydroxylcarboxamide in the form of a colorless solid.

0.51 g of potassium carbonate was added to a mixed solution of 1.3 g of the compound obtained above in 13 mL of methanol and 1.3 mL of water, and the system was stirred for 6 hours at room temperature. The solvent was distilled off under reduced pressure, after which ethyl acetate was added, and the organic layer was washed with saturated brine, dried with magnesium sulfate, and subjected to reduced-pressure solvent distillation. The residue was refined by silica gel column chromatography (35% ethyl acetate/hexane) to obtain 1.1 g of 4,5-dihydro-8-(methylamino)naphtho[1,2-b]thiophene-2-N,O-dimethylhydroxylcarboxamide (compound 4-16) in the form of a light brown oily substance.

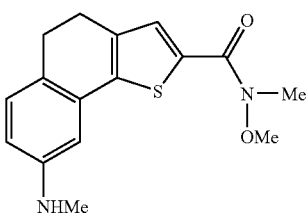

Compound 4-16

¹H NMR (200 MHz, CDCl₃) δ (ppm):2.73-2.94 (m, 4H), 2.88 (s, 3H), 3.39 (s, 3H), 3.82 (s, 3H), 6.52 (dd, J=2.5, 8.0 Hz, 1H), 6.71 (d, J=2.5 Hz, 1H), 7.06 (d, J=8.0 Hz, 1H), 7.76 (s, 1H)

EXAMPLES

Example 1

Method A 13 mL of a diethyl ether solution of 3M methyl magnesium bromide was added under ice cooling and nitrogen replacement to a 100 mL tetrahydrofuran solution of 4.7 g of the compound obtained in Reference Example 9 (4-1), and the system was stirred for 3 hours at the same temperature. After the reaction, 10% hydrochloric acid was added under ice cooling, extraction was performed with ethyl acetate, the organic layer was washed with saturated brine, dried with magnesium sulfate, and subjected to reduced-pressure solvent distillation, and the residue was refined by silica gel column chromatography (25% ethyl acetate/hexane), after which it was recrystallized with ethanol to obtain 3.8 g of 2-acetyl-4,5-dihydro-6,8-dimethylnaphtho[1,2-b]thiophene (Table 6-1) in the form of yellow crystals.

Method B 1.3 mL of phosphorus oxychloride was added dropwise to 1.6 mL of dimethylformamide under ice cooling, after which the system was brought up to room temperature and stirred for 30 minutes. To this was added at room temperature a 50 mL chloroform solution of 1.8 g of 5,7-dimethyltetralone, and the system was refluxed under heating overnight. After the reaction, water was added and the system was stirred for 30 minutes, after which the organic layer was washed first with a saturated sodium hydrogencarbonate aqueous solution and then with saturated brine, dried with magnesium sulfate, and then subjected to reduced-pressure solvent distillation, and the residue was refined by silica gel column chromatography (5% ethyl acetate/hexane) to obtain 2.0 g of 1-chloro-2-formyl-3,4-dihydronaphthalene in the form of a brown solid.

Next, 1.4 mL of triethylamine was added dropwise to a 10 mL ethanol solution of 0.9 g of 2,5-dihydroxy-2,5-dimethyl-1,4-dithiane, and the system was stirred for 30 minutes at room temperature. To this was added at room temperature a 10 mL ethanol solution of the 1-chloro-2-formyl-3,4-dihydronaphthalene obtained previously, and the system was refluxed under heating overnight. After the reaction, reduced-pressure solvent distillation was performed, first water and then 2M a sodium hydroxide aqueous solution were added under ice cooling, and extraction was performed with ethyl acetate. The organic layer was washed first with a saturated ammonium chloride aqueous solution and then with saturated brine, dried with magnesium sulfate, and subjected to reduced-pressure solvent distillation, and the residue was refined by silica gel column chromatography (20% ethyl acetate/hexane) and then recrystallized with ethanol to obtain 1.6 g of 2-acetyl-4,5-dihydro-6,8-dimethylnaphtho[1,2-b]thiophene (Table 6-1) in the form of yellow crystals.

The compounds of Examples 2 to 36 shown in Tables 6-1 to 6-7 were then obtained by the same method.

TABLE 6-1

(5)

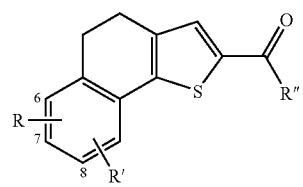

| Example | R | R' | R" | Data |
|---|---|---|---|---|
| 1 | 6-Me | 8-Me | Me | MS m/z: 257(M + H)⁺ ¹H NMR(200 MHz, CDCl₃) δ (ppm): 2.29(s, 3H), 2.31(s, 3H), 2.54(s, 3H), 2.73-2.95(m, 4H), 6.96(s, 1H), 7.18(s, 1H), 7.50(s, 1H) |
| 2 | 7-Me | 8-Me | Me | MS m/z: 257(M + H)⁺ ¹H NMR(200 MHz, CDCl₃) δ (ppm): 2.26(s, 3H), 2.27(s, 3H), 2.54(s, 3H), 2.68-3.10(m, 4H), 7.03(s, 1H), 7.25(s, 1H), 7.49(s, 1H) |
| 3 | 8-Me | H | Me | MS m/z: 243(M + H)⁺ ¹H NMR(300 MHz, CDCl₃) δ (ppm): 2.35(s, 3H), 2.54(s, 3H), 2.75-2.98(m, 4H), 7.06(d, J=9.0 Hz, 1H), 7.14(d, J=9.0 Hz, 1H), 7.50(s, 1H) |
| 4 | 6-OMe | H | Me | MS m/z: 259(M + H)⁺ ¹H NMR(200 MHz, CDCl₃) δ (ppm): 2.56(s, 3H), 2.77-3.03(m, 4H), 3.90(s, 3H), 6.85(d, J=6.8 Hz, 1H), 7.11(d, J=6.8 Hz, 1H), 7.21(d, J=6.8 Hz, 1H), 7.51(s, 1H) |
| 5 | 7-OMe | H | Me | MS m/z: 259(M + H)⁺ ¹H NMR(200 MHz, CDCl₃) δ (ppm): 2.54(s, 3H), 2.74-3.05(m, 4H), 3.85(s, 3H), 6.72-6.90(s, 2H), 7.41(d, J=8.8 Hz, 1H), 7.49(s, 1H) |

TABLE 6-2

| Example | R | R' | R" | Data |
|---|---|---|---|---|
| 6 | 8-OMe | H | Me | MS m/z: 259(M+H)⁺ ¹H NMR(200MHz, CDCl₃) δ(ppm): 2.55(s, 3H), 2.77-2.96(m, 4H), 3.84(s, 3H), 6.79(dd, J=8.4, 2.7Hz, 1H), 7.01(d, J=2.7Hz, 1H), 7.15(d, J=8.4Hz, 1H), 7.49(s, 1H) |

TABLE 6-2-continued

| Example | R | R' | R" | Data |
|---|---|---|---|---|
| 7 | 6-OBzl | H | Me | MS m/z: 357(M+Na)$^+$<br>$^1$H NMR(200MHz, CDCl$_3$) δ(ppm):<br>2.77(s, 3H), 2.77-3.12(m, 4H), 5.13(s, 2H),<br>6.91(dd, J=1.8, 7.9Hz, 1H), 7.10-7.53(m, 8H) |
| 8 | 7-OBzl | H | Me | MS m/z: 335(M+H)$^+$<br>$^1$H NMR(300MHz, CDCl$_3$) δ(ppm):<br>2.54(s, 3H), 2.77-2.99(m, 4H), 5.09(s, 2H),<br>6.84(d, J=2.5Hz, 1H), 6.87(s, 1H), 7.31-7.47(m, 6H),<br>7.48(s, 1H) |
| 9 | 6,7-Ethylenedioxy | | Me | MS m/z: 309(M+Na)$^+$<br>$^1$H NMR(200MHz, CDCl$_3$) δ(ppm):<br>2.53(s, 1H), 2.76-2.90(m, 4H), 4.29(s, 4H),<br>6.75(s, 1H), 7.03(s, 1H), 7.47(s, 1H) |
| 10 | 8-F | H | Me | MS m/z: 269(M+Na)$^+$<br>$^1$H NMR(200MHz, CDCl$_3$) δ(ppm):<br>2.55(s, 3H), 2.74-3.08(m, 4H),<br>6.77-7.06(m, 1H), 7.07-7.32(m, 2H), 7.50(s, 1H) |
| 11 | 7-F | 8-OMe | Me | MS m/z: 299(M+Na)$^+$<br>$^1$H NMR(200MHz, CDCl$_3$) δ(ppm):<br>2.55(s, 3H), 2.74-3.01(m, 4H), 3.93(s, 3H),<br>6.89-7.11(m, 2H), 7.50(s, 1H) |

TABLE 6-3

| Example | R | R' | R" | Data |
|---|---|---|---|---|
| 12 | 6-Me | 8-Me | Et | MS m/z: 271(M+H)$^+$<br>$^1$H NMR(300MHz, CDCl$_3$) δ(ppm):<br>1.25(t, J=7.3Hz, 3H), 2.30(s, 3H), 2.32(s, 3H),<br>2.76-2.88(m, 4H), 2.91(q, J=7.3Hz, 2H),<br>6.95(s, 1H), 7.17(s, 1H), 7.50(s, 1H) |
| 13 | 6-Me | 8-Me | Pr | MS m/z: 285(M+H)$^+$<br>$^1$H NMR(300MHz, CDCl$_3$) δ(ppm): 1.02(t,<br>J=7.5Hz, 3H), 1.70-1.89(m, 2H), 2.30(s,<br>3H), 2.32(s, 3H), 2.75-2.95(m, 6H),<br>6.95(s, 1H), 7.17(s, 1H), 7.50(s, 1H) |
| 14 | 6-Me | 8-Me | Pr$^i$ | MS m/z: 285(M+H)$^+$<br>$^1$H NMR(300MHz, CDCl$_3$) δ(ppm):<br>1.26(d, J=6.8Hz, 6H), 2.30(s, 3H), 2.32(s, 3H),<br>2.77-2.93(m, 4H), 3.25-3.47(m, 1H),<br>6.95(s, 1H), 7.18(s, 1H), 7.52(s, 1H) |
| 15 | 8-Et | H | Me | MS m/z: 257(M+H)$^+$<br>$^1$H NMR(300MHz, CDCl$_3$) δ(ppm):<br>1.26(t, J=7.6Hz, 3H), 2.55(s, 3H), 2.66(q,<br>J=7.6Hz, 2H), 2.78-3.01(m, 4H), 7.08(d,<br>J=8.0Hz 1H), 7.15(d, J=8.0Hz 1H),<br>7.28(s, 1H), 7.50(s, 1H) |
| 16 | 8-Pr | H | Me | MS m/z: 293(M+Na)$^+$<br>$^1$H NMR(300MHz, CDCl$_3$) δ(ppm): 0.97(t,<br>J=7.3Hz, 3H), 1.67(m, 2H), 2.52-2.65(m,<br>5H), 2.78-3.01(m, 4H), 7.07(d, J=9.0H, 1H),<br>7.16(d, J=9.0H, 1H), 7.29(s, 1H),<br>7.51(s, 1H) |

TABLE 6-4

| Example | R | R' | R" | Data |
|---|---|---|---|---|
| 17 | 8-Pr$^i$ | H | Me | MS m/z: 271(M+H)$^+$<br>$^1$H NMR(300MHz, CDCl$_3$) δ(ppm):<br>1.27(d, J=6.8Hz, 6H), 2.55(s, 3H),<br>2.79-2.99(m, 4H), 7.08-7.20(m, 2H), 7.33(s, 1H),<br>7.50(s, 1H) |
| 18 | 8-cycloHexyl | H | Me | MS m/z: 311(M+H)$^+$<br>$^1$H NMR(300MHZ, CDCl$_3$) δ(ppm):<br>1.18-1.52(m, 5H) 1.70-1.96(m, 5H)<br>2.44-2.57(m, 4H) 2.78-2.98(m, 4H) 7.09(d, J=6.0Hz,<br>1H) 7.16(d, J=6.0Hz, 1H) 7.31(s, 1H)<br>7.49(s, 1H) |
| 19 | 8-Cl | H | Me | MS m/z: 263(M+H)$^+$<br>$^1$H NMR(300MHz, CDCl$_3$) δ(ppm):<br>2.55(s, 3H), 2.79-2.99(m, 4H), 7.13-7.22(m,<br>2H), 7.42(d, J=1.9Hz, 1H), 7.50(s, 1H) |
| 20 | 7-Me | 8-OMe | Me | MS m/z: 295(M+Na)$^+$<br>$^1$H NMR(300MHz, CDCl$_3$) δ(ppm):<br>2.22(s, 3H), 2.55(s, 3H), 2.72-2.92(m, 4H),<br>3.87(s, 3H), 6.90(s, 1H) 7.01(s, 1H),<br>7.49(s, 1H) |
| 21 | 6-F | 8-Me | Me | MS m/z: 261(M+H)$^+$<br>$^1$H NMR(200MHz, CDCl$_3$) δ(ppm): 2.35(s, |

TABLE 6-4-continued

| Example | R | R' | R" | Data |
|---|---|---|---|---|
| | | | | 3H), 2.55(s, 3H), 2.73-3.07(m, 4H), 6.82(d, J=10.1Hz, 1H), 7.08(s, 1H), 7.49(s, 1H) |
| 22 | 7-F | 8-Me | Me | MS m/z: 283(M+Na)$^+$<br>$^1$H NMR(200MHz, CDCl$_3$) δ(ppm): 2.54(s, 3H), 2.73-2.99(m, 4H), 6.89(d, J=10.1Hz, 1H), 7.27(d, J=7.5Hz, 1H), 7.48(s, 1H) |
| 23 | 6-F | 8-OMe | Me | MS m/z: 299(M+Na)$^+$<br>$^1$H NMR(200MHz, CDCl$_3$) δ(ppm): 2.56(s, 3H), 2.72-3.02(m, 4H), 3.83(s, 3H), 6.57(dd, J=11.0, 2.4Hz, 1H), 6.82(d, J=2.4Hz, 1H), 7.50(s, 1H) |

TABLE 6-5

| Example | R | R' | R" | Data |
|---|---|---|---|---|
| 24 | 7-F | H | Me | MS m/z: 247(M+H)$^+$<br>$^1$H NMR(200MHz, CDCl$_3$) δ(ppm): 2.55(s, 3H), 2.73-3.10(m, 4H), 6.75-7.07(m, 2H), 7.36-7.47(m, 1H), 7.49(s, 1H) |
| 25 | 7-Cl | H | Me | MS m/z: 263(M+H)$^+$<br>$^1$H NMR(200MHz, CDCl$_3$) δ(ppm): 2.55(s, 3H), 2.75-3.06(m, 4H), 7.13-7.32(m, 2H), 7.38-7.60(m, 2H) |
| 26 | 7-Me | H | Me | MS m/z: 265(M+Na)$^+$<br>$^1$H NMR(200MHz, CDCl$_3$) δ(ppm): 2.35(s, 3H), 2.55(s, 3H), 2.73-3.03(m, 4H), 6.95-7.15(m, 2H), 7.36(d, J=8.4Hz, 1H), 7.49(s, 1H) |
| 27 | 7-OEt | H | Me | MS m/z: 295(M+Na)$^+$<br>$^1$H NMR(300MHz, CDCl$_3$) δ(ppm): 1.43(t, J=7.0Hz, 3H), 2.53(s, 3H), 2.78-2.99(m, 4H), 4.06(q, J=7.0Hz, 2H), 6.73-6.82(m, 2H), 7.39(d, J=9.2Hz, 1H), 7.48(s, 1H) |
| 28 | 7-O-cycloHexylmethyl | H | Me | MS m/z: 363(M+Na)$^+$<br>$^1$H NMR(300MHz, CDCl$_3$) δ(ppm): 0.95-1.40(m, 5H), 1.65-1.94(m, 6H), 2.53(s, 3H), 2.72-2.99(m, 4H), 3.77(d, J=6.2Hz, 2H), 6.73-6.81(m, 2H), 7.38(d, J=9.0Hz, 1H), 7.48(s, 1H) |
| 29 | 7-OPr | H | Me | MS m/z: 309(M+Na)$^+$<br>$^1$H NMR(300MHz, CDCl$_3$) δ(ppm): 1.05(t, J=7.4Hz, 3H), 1.82(tq, J=7.4, 7.0Hz, 2H), 2.53(s, 3H), 2.77-2.98(m, 4H), 3.95(t, J=7.0Hz, 2H), 6.73-6.82(m, 2H), 7.39(d, J=9.0Hz, 1H), 7.48(s, 1H) |

TABLE 6-6

| Example | R | R' | R" | Data |
|---|---|---|---|---|
| 30 | 7-OBz | H | Me | MS m/z: 371(M+Na)$^+$<br>$^1$H NMR(300MHz, CDCl$_3$) δ(ppm): 2.56(s, 3H), 2.82-3.06(m, 4H), 7.07-7.16(m, 2H), 7.49-7.56(m, 4H), 7.61-7.70(m, 1H), 8.16-8.25(m, 2H) |
| 31 | 7-OPr$^i$ | H | Me | MS m/z: 309(M+Na)$^+$<br>$^1$H NMR(300MHz, CDCl$_3$) δ(ppm): 1.36(d, J=6.1Hz, 6H), 2.54(s, 3H), 2.78-2.99(m, 4H), 4.52-4.66(m, 1H), 6.73-6.81(m, 1H), 7.39(d, J=9.2Hz, 1H), 7.49(s, 1H) |
| 32 | 7-NHTFA | H | Me | MS m/z: 340(M+H)$^+$<br>$^1$H NMR(200MHz, CDCl$_3$) δ(ppm): 2.56(s, 3H), 2.77-3.06(m, 4H), 7.31-7.41(m, 2H), 7.42-7.54(m, 1H), 7.59(s, 1H) |
| 33 | 8-NMe$_2$ | H | Me | MS m/z: 294(M+Na)$^+$<br>$^1$H NMR(200MHz, CDCl$_3$) δ(ppm): 2.54(s, 3H), 2.75-2.93(m, 4H), 2.95(s, 6H), 6.67(dd, J=2.5, 8.0Hz, 1H), 6.83(d, J=2.5Hz, 1H), 7.11(d, J=8.0Hz, 1H), 7.49(s, 1H) |
| 34 | 8-NEt$_2$ | H | Me | MS m/z: 322(M+Na)$^+$<br>$^1$H NMR(200MHz, CDCl$_3$) δ(ppm): 1.18(t, J=8.5Hz, 6H), 2.55(s, 3H), 2.74-2.94(m, 4H), 3.38(q, J=8.5Hz, 4H), 6.61(dd, J=2.5, 8.0Hz, 1H), 6.79(d, J=2.5Hz, 1H), 7.08(d, J=8.0Hz, 1H), 7.50(s, 1H) |

TABLE 6-7

| Example | R | R' | R" | Data |
|---|---|---|---|---|
| 35 | 8-NBzl₂ | H | Me | MS m/z: 446(M+Na)⁺<br>¹H NMR(200MHz, CDCl₃) δ(ppm): 2.52(s, 3H), 2.71-2.92(m, 4H), 4.67(s, 4H), 6.63(dd, J=2.5, 8.0Hz, 1H), 6.87(d, J=2.5Hz, 1H), 7.04(d, J=8.0Hz, 1H), 7.16-7.42(m, 10H), 7.47(s, 1H) |
| 36 | 8-NHMe | H | Me | MS m/z: 280(M+Na)⁺<br>¹H NMR(200MHz, CDCl₃) δ(ppm): 2.55(s, 3H), 2.73-2.93(m, 4H), 2.86(s, 3H), 3.63-3.84(br, 1H), 6.53(dd, J=2.5, 8.0Hz, 1H), 6.72(d, J=2.5Hz, 1H), 7.06(d, J=8.0Hz, 1H), 7.49(s, 1H) |

Example 37

10% palladium-carbon was added to a mixed solution of 210 mg of the compound obtained in Example 7 in 4 mL of ethanol and 2 mL of tetrahydrofuran, and the system was stirred overnight at room temperature under hydrogen replacement. After the reaction, the system was filtered through celite, and reduced-pressure solvent distillation was performed to obtain 30 mg of 2-acetyl-4,5-dihydro-6-hydroxynaphtho[1,2-b]thiophene in the form of a colorless solid.

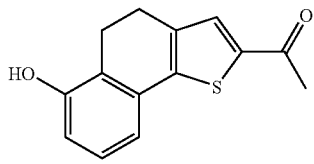

MS m/z: 267 (M+Na)⁺

¹H NMR (200 MHz, CDCl₃) δ (ppm):2.56 (s, 3H), 2.81-3.02 (m, 4H), 4.84 (s, 1H), 6.76 (t, J=1.8 Hz, 1H), 7.11 (s, 1H), 7.14 (d, J=1.8 Hz, 1H), 7.51 (s, 1H)

Example 38

0.46 mL of a 1M boron tribromide dichloromethane was added under nitrogen replacement and cooling to −78° C. to a 2 mL dichloromethane solution of 100 mg of the compound obtained in Example 6, and the system was brought up to room temperature and stirred overnight. After the reaction, a saturated sodium hydrogencarbonate aqueous solution was added under ice cooling, extraction was performed with ethyl acetate, and the organic layer was washed with saturated brine, dried with magnesium sulfate, and subjected to reduced-pressure solvent distillation, and the residue was refined by silica gel column chromatography (35% ethyl acetate/hexane) to obtain 40 mg of 2-acetyl-4,5-dihydro-8-hydroxynaphtho[1,2-b]thiophene in the form of a brown solid.

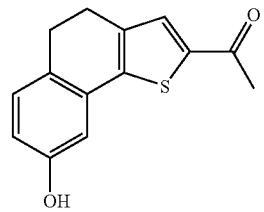

MS m/z: 267 (M+Na)⁺

¹H NMR (200 MHz, CDCl₃) δ (ppm):2.59 (s, 3H), 2.80-2.94 (m, 4H), 5.76 (br, 1H), 6.74 (dd, J=2.6, 8.4 Hz, 1H), 7.10-7.14 (m, 2H), 7.52 (s, 1H)

Example 39

A potassium hydroxide aqueous solution (6.8 g potassium hydroxide, 60 mL water) was added dropwise to a mixed solution of 21.25 g of the compound obtained in Example 30 in 200 mL of ethanol and 200 mL of tetrahydrofuran, and the system was stirred for 1 hour at room temperature. After the reaction, reduced-pressure solvent distillation was performed, and 12M hydrochloric acid was added. The precipitated crystals were filtered off, dried, and recrystallized with ethanol to obtain 12.2 g of 2-acetyl-4,5-dihydro-7-hydroxynaphtho[1,2-b]thiophene in the form of brown crystals.

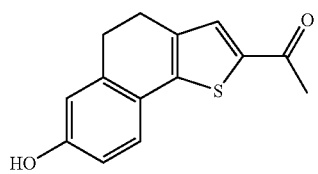

MS m/z: 267 (M+Na)⁺

¹H NMR (300 MHz, dmso-d₆) δ (ppm): 2.67-2.94 (m, 4H) 6.62-6.75 (m, 2 H) 7.30 (d, J=8.1 Hz, 1 H) 7.77 (s, 1 H) 9.79 (s, 1 H)

Example 40

0.73 g of potassium carbonate was added to a mixed solution of 1.2 g of the compound obtained in Example 32 in 10 mL of water and 10 mL of methanol, and the system was stirred for overnight at room temperature. Reduced-pressure solvent distillation was performed, water was added, and extraction was performed with ethyl acetate. The extracted organic layer was washed with saturated brine, dried with magnesium sulfate, and subjected to reduced-pressure solvent distillation to obtain 1.0 g of 2-acetyl-4,5-dihydro-7-aminonaphtho[1,2-b]thiophene in the form of a brown powder.

0.78 mL of methyl iodide and 1.04 g of sodium hydrogencarbonate were added under ice cooling to a 10 mL dimethylformamide solution of 0.6 g of the compound obtained above, and the system was stirred overnight at room temperature, and then stirred for another 10 hours at 100° C. After the reaction, water was added, extraction was performed with ethyl acetate, the organic layer was washed first with water and then with saturated brine, dried with magnesium sulfate, and then subjected to reduced-pressure solvent distillation. The residue thus obtained was refined by silica gel column chromatography (10% ethyl acetate/hexane) to obtain 50 mg of 2-acetyl-4,5-dihydro-7-(dimethylamino)naphtho[1,2-b]thiophene in the form of a yellow powder.

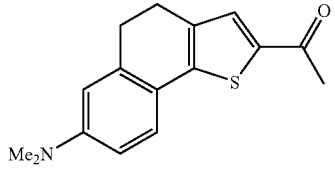

MS m/z: 272 (M+H)$^+$ $^1$H NMR (200 MHz, CDCl$_3$) δ (ppm):2.52 (s, 3H), 2.72-2.98 (m, 4H), 3.01 (s, 6H), 6.51-6.68 (m, 2H), 7.36 (d, J=8.8 Hz, 1H), 7.46 (s, 1H)

Example 41

0.22 mL of methyl iodide and 0.61 g of potassium carbonate were added to a 10 mL dimethylformamide solution of 1 g of the compound obtained in Example 32, and the system was stirred overnight at 80° C. After the reaction, water was added, extraction was performed with ethyl acetate, and the organic layer was washed first with water and then with saturated brine, dried with magnesium sulfate, and subjected to reduced-pressure solvent distillation. The residue thus obtained was dissolved in 50 mL of water and 50 mL of methanol, 0.78 g of potassium carbonate was added to the resulting mixed solution, and the system was stirred overnight at room temperature. Reduced-pressure solvent distillation was performed, water was added, and extraction was performed with ethyl acetate. The extracted organic layer was washed with saturated brine, dried with magnesium sulfate, and then subjected to reduced-pressure solvent distillation. The residue thus obtained was refined by silica gel column chromatography (10% ethyl acetate/hexane) to obtain 0.61 g of 2-acetyl-4,5-dihydro-7-(methylamino)naphtho[1,2-b]thiophene in the form of a yellow powder.

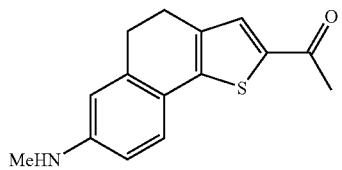

MS m/z: 258 (M+H)$^+$ $^1$H NMR (200 MHz, CDCl$_3$) δ (ppm):2.52 (s, 3H), 2.64-3.06 (m, 7H), 6.38-6.59 (m, 2 H), 7.31 (d, J=8.4 Hz, 1H), 7.45 (s, 1H)

The compound of Example 42 was obtained by the same method.

Example 42

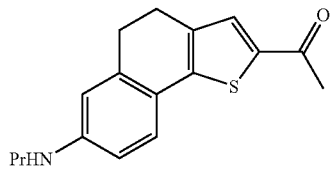

MS m/z: 286 (M+H)$^+$ $^1$H NMR (200 MHz, CDCl$_3$) δ (ppm):1.01 (t, J=7.3 Hz, 3H), 1.57-1.77 (m, 2H), 2.52 (s, 3H), 2.70-2.97 (m, 4H), 3.12 (t, J=7.0 Hz, 2H), 6.39-6.55 (m, 2 H), 7.29 (d, J=8.4 Hz, 1H), 7.45 (s, 1H)

Example 43

0.73 g of potassium carbonate was added to a mixed solution of 1.2 g of the compound obtained in Example 32 in 10 mL of water and 10 mL of methanol, and the system was stirred overnight at room temperature. Reduced-pressure solvent distillation was performed, water was added, and extraction was performed with ethyl acetate. The extracted organic layer was washed with saturated brine, dried with magnesium sulfate, and subjected to reduced-pressure solvent distillation to obtain 1.0 g of 2-acetyl-4,5-dihydro-7-aminonaphtho[1,2-b]thiophene in the form of a brown powder.

0.06 mL acetic anhydride was added to a 5 mL pyridine solution of 0.1 g of the compound obtained above, and the system was stirred overnight at room temperature. After the reaction, water was added, and extraction was performed with ethyl acetate. The extracted organic layer was washed first with 1M hydrochloric acid and then with saturated brine, dried with magnesium sulfate, and then subjected to reduced-pressure solvent distillation to obtain 90 mg of 2-acetyl-4,5-dihydro-7-acetamidenaphtho[1,2-b]thiophene in the form of an orange powder.

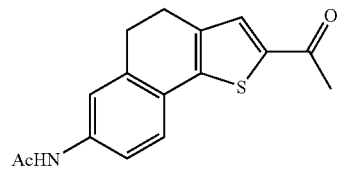

MS m/z:286 (M+H)$^+$ $^1$H NMR (200 MHz, CDCl$_3$) δ (ppm):2.20 (s, 3H), 2.54 (s, 3H), 2.73-3.07 (m, 4H), 7.16-7.32 (m, 2 H), 7.40 (d, J=8.0 Hz, 1H), 7.48 (s, 1H), 7.53-7.65 (m, 1H)

Example 44

0.46 mL of butyl iodide and 0.83 g of potassium carbonate were added to a 10 mL dimethylformamide solution of 0.5 g of the compound obtained in Example 39, and the system was stirred for 2 hours at 80° C. After the reaction, water was added and extraction was performed with ethyl acetate. The extracted organic layer was washed with saturated brine, dried with magnesium sulfate, and then subjected to reduced-pressure solvent distillation. The residue thus obtained was refined by silica gel column chromatography (10% ethyl acetate/hexane) and then recrystallized with ethanol to obtain 0.48 g of 2-acetyl-4,5-dihydro-7-(n-butyloxy)naphtho[1,2-b]thiophene (Table 7-1) in the form of yellow crystals.

The compounds of Examples 45 to 55 shown in Tables 7-1 to 7-3 were obtained by the same method.

TABLE 7-1

(5)

| Example | R | R' | Data |
|---|---|---|---|
| 44 | 7-OBu | H | MS m/z: 323(M + Na)⁺<br>¹H NMR(200 MHz, CDCl₃) δ (ppm):<br>0.98(t, J=7.3 Hz, 3H), 1.36-1.62(m, 2H),<br>1.66-1.91(m, 2H), 2.53(s, 3H), 2.72-3.07(m, 4H),<br>3.98(t, J=6.4 Hz, 2H), 6.67-6.88(m, 2H),<br>7.38(d, J=9.2 Hz, 1H), 7.47(s, 1H) |
| 45 | 7-OBuⁱ | H | MS m/z: 301(M + H)⁺<br>¹H NMR(300 MHz, CDCl₃) δ (ppm):<br>1.03(d, J=6.8 Hz, 6H), 2.02-2.16(m, 1H),<br>2.53(s, 3H), 2.76-2.99(m, 4H), 3.74(d, J=6.5 Hz, 2H), 6.72-6.81(m, 2H), 7.39(d, J=8.7 Hz, 1H), 7.48(s, 1H) |
| 46 | 7-O-Pentyl | H | MS m/z: 314(M + H)⁺<br>¹H NMR(200 MHz, CDCl₃) δ (ppm):<br>0.81-1.04(m, 3H), 1.26-1.55(m, 4H),<br>1.65-1.96(m, 2H), 2.53(s, 3H), 2.70-3.08(m, 4H),<br>3.98(t, J=6.6 Hz, 2H), 6.61-6.90(m, 2H),<br>7.39(d, J=8.8 Hz, 1H), 7.47(s, 1H) |
| 47 | 7-O-Hexyl | H | MS m/z: 351(M + Na)⁺<br>¹H NMR(200 MHz, CDCl₃) δ (ppm):<br>0.83-0.98(m, 3H), 1.17-1.55(m, 6H),<br>1.64-1.91(m, 2H), 2.53(s, 3H), 2.72-3.10(m, 4H),<br>3.98(t, J=6.6 Hz, 2H), 6.63-6.89(m, 2H),<br>7.38(d, J=9.3 Hz, 1H), 7.47(s, 1H) |

TABLE 7-2

| Example | R | R' | Data |
|---|---|---|---|
| 48 | 7-O-cyclopropylmethyl | H | MS m/z: 299(M + H)⁺<br>¹H NMR(300 MHz, CDCl₃) δ (ppm):<br>0.32-0.39(m, 2H), 0.62-0.71(m, 2H),<br>1.20-1.36(m, 1H), 2.53(s, 3H),<br>2.77-2.99(m, 4H), 3.83(d, J=7.0 Hz, 2H),<br>6.74-6.82(m, 2H), 7.39(d, J=8.7 Hz, 1H),<br>7.48(s, 1H) |
| 49 | 7-O-cyclopentyl | H | MS m/z: 335(M + Na)⁺<br>¹H NMR(200 MHz, CDCl₃) δ (ppm):<br>1.49-2.00(m, 8H), 2.53(s, 3H),<br>2.72-3.02(m, 4H), 4.62-4.90(m, 1H),<br>6.61-6.85(m, 2H), 7.37(d, J=9.2 Hz, 1H),<br>7.47(s, 1H) |
| 50 | 7-O-neopentyl | H | MS m/z: 315(M + H)⁺<br>¹H NMR(200 MHz, CDCl₃) δ (ppm):<br>1.04(s, 9H), 2.53(s, 3H), 2.69-3.05(m, 4H), 3.61(s, 2H), 6.65-6.88(m, 2H)<br>7.38(d, J=8.8 Hz, 1H), 7.47(s, 1H) |

TABLE 7-2-continued

| Example | R | R' | Data |
|---|---|---|---|
| 51 | 7-O-allyl | H | MS m/z: 285(M + H)⁺<br>¹H NMR(300 MHz, CDCl₃) δ (ppm):<br>2.54(s, 3H), 2.77-3.00(m, 4H),<br>4.54-4.60(m, 2H), 5.28-5.35(m, 1H),<br>5.38-5.48(m, 1H), 5.98-6.14(m, 1H),<br>6.77-6.83(m, 2H), 7.40 (d, J=9.0 Hz, 1H),<br>7.48(s, 1H) |
| 52 | 7-O-methallyl | H | MS m/z: 298(M + H)⁺<br>¹H NMR(300 MHz, CDCl₃) δ (ppm):<br>1.84(s, 1H), 2.53(s, 3H), 2.78-2.98(m, 4H), 4.46(s, 2H), 4.99-5.02(m, 1H),<br>5.07-5.12(m, 1H), 6.77-6.83(m, 2H),<br>7.39(d, J=8.9 Hz, 1H), 7.48(s, 1H) |

TABLE 7-3

| Example | R | R' | Data |
|---|---|---|---|
| 53 | 7-O-propargyl | H | MS m/z: 283(M + H)⁺<br>¹H NMR(300 MHz, CDCl₃) δ (ppm):<br>2.52-2.58(m, 4H), 2.78-3.04(m, 4H),<br>4.67-4.78(m, 2H), 6.81-46.91(m, 2H),<br>7.38-7.46(m, 1H), 7.49(s, 1H) |
| 54 | 8-OEt | H | MS m/z: 295(M + Na)⁺<br>¹H NMR(200 MHz, CDCl₃) δ (ppm):<br>1.43(t, J=6.8 Hz, 3H), 2.55(s, 3H),<br>2.73-2.97(m, 4H), 4.06(q, J=6.8 Hz, 2H),<br>6.78(dd, J=8.4, 2.6 Hz, 1H), 6.99(d, J=2.6 Hz, 1H), 7.13(d, J=18.4 Hz, 1H),<br>7.49(s, 1H) |
| 55 | 8-OBzl | H | MS m/z: 357(M + Na)⁺<br>¹H NMR(200 MHz, CDCl₃) δ (ppm):<br>2.55(s, 3H), 2.68-3.14(m, 4H), 5.09(s, 2H), 6.86(dd, J=8.1, 2.6 Hz, 1H), 7.09(d, J=2.6 Hz, 1H), 7.14(d, J=8.1 Hz, 1H),<br>7.28-7.51(m, 6H) |

Example 56

5 mL of trifluoromethanesulfonic anhydride was added under ice cooling to a 50 mL pyridine solution of 5 g of the compound obtained in Example 39, and the system was stirred for 2 hours at the same temperature. After the reaction, water was added at the same temperature, and extraction was performed with ethyl acetate. The extracted organic layer was washed with saturated brine, dried with magnesium sulfate, and then subjected to reduced-pressure solvent distillation. The residue thus obtained was refined by silica gel column chromatography (25% ethyl acetate/hexane) to obtain 6.24 g of 2-acetyl-4,5-dihydro-7-(trifluoromethanesulfonyloxy)naphtho[1,2-b]thiophene in the form of a yellow powder.

A suspension of 1.0 g of the compound obtained above, 0.3 g of n-butylboronic acid, 0.19 g of [1,1-bis(diphenylphosphino)ferrocene]palladium(II)dichloride, 1.1 g of potassium carbonate, and 1.5 g of silver oxide in 10 mL of tetrahydrofuran was stirred for 20 hours at 80° C. under nitrogen replacement. After the reaction, 15 mL of 30% aqueous hydrogen peroxide and 15 mL of a 10% sodium hydroxide aqueous solution were added under ice cooling, and extraction was performed with ethyl acetate. The extracted organic layer was washed with saturated brine, dried with magnesium sulfate, and then subjected to reduced-pressure solvent distillation. The residue thus obtained was refined by silica gel column chromatography (10% ethyl acetate/hexane) to obtain 0.18 g of 2-acetyl-4,5-dihydro-7-(n-butyl)naphtho[1,2-b]thiophene (Table 8) in the form of a yellow powder.

The compounds of Examples 57 and 58 shown in Table 8 were obtained by the same method.

jected to reduced-pressure solvent distillation, and the residue was refined by silica gel column chromatography (25% ethyl acetate/hexane) to obtain 0.50 g of 2-(2-hydroxyethyl)-4,5-dihydro-6,8-dimethylnaphtho[1,2-b]thiophene (Table 9-1) in the form of a brown solid.

The compounds of Examples 60 to 104 shown in Tables 9-1 to 9-11 were obtained by the same method.

TABLE 8

(5)

| Example | R | R" | Data |
|---|---|---|---|
| 56 | 7-Bu | H | MS m/z 285(M + H)+<br>1H NMR(200 MHz, CDCl3) δ (ppm):<br>0.94(t, J=7.3 Hz, 3H), 1.23-1.49(m, 2H),<br>1.50-1.72(m, 2H), 2.54(s, 3H), 2.52-2.68(m, 2H), 2.73-3.05(m, 4H), 7.01-7.13(m, 2H), 7.38(d, J=8.4 Hz, 1H), 7.49(s, 1H) |
| 57 | 7-Pr | H | MS m/z: 271(M + H)+<br>1H NMR(200 MHz, CDCl3) δ (ppm):<br>0.96(t, J=7.3 Hz, 3H), 1.56-1.76(m, 2H),<br>2.54(s, 3H), 2.52-2.62(m, 2H), 2.75-3.03(m, 4H), 7.02-7.11(m, 2H), 7.38(d, J=8.4 Hz, 1H), 7.49(s, 1H) |
| 58 | 7-Et | H | MS m/z: 279(M + Na)+<br>1H NMR(200 MHz, CDCl3) δ (ppm):<br>1.25(t, J=7.6 Hz, 3H), 2.54(s, 3H), 2.64(q, J=7.6 Hz, 2H), 2.79-3.00(m, 4H), 7.03-7.14(m, 2H), 7.39(d, J=8.4 Hz, 1H), 7.49(s, 1H) |

Example 59

0.18 g of sodium boron hydride was added under nitrogen replacement and ice cooling to a 10 mL ethanol solution of 0.50 g of the compound obtained in Example 1, and the system was stirred for 2 hours at room temperature. After the reaction, reduced-pressure solvent distillation was performed, a saturated ammonium chloride aqueous solution was added under ice cooling, extraction was performed with ethyl acetate, and the organic layer was washed with saturated brine, dried with magnesium sulfate, and then sub-

TABLE 9-1

(6)

| Example | R | R' | R" | Data |
|---|---|---|---|---|
| 59 | 6-Me | 8-Me | Me | MS m/z: 281(M + Na)+<br>1H NMR(200 MHz, CDCl3) δ (ppm):<br>1.62(d, J=8.0 Hz, 3H), 2.28(s, 3H), 2.30(s, 3H), 2.67-2.96(m, 4H), 4.96-5.21(m, 1H), 6.79(s, 1H), 6.86(s, 1H), 7.05(s, 1H) |
| 60 | 6-OMe | H | Me | MS m/z: 242(M − OH)+<br>1H NMR(200 MHz, CDCl3) δ (ppm):<br>1.62(d, J=6.6 Hz, 3H), 2.66–3.06 (m, 4H), 3.85(s, 3H), 4.12(m, 1H), 6.68–6.84 (m, 2H), 6.92–7.03(m, 1H), 7.08-7.22 (m, 1H) |
| 61 | 7-OMe | H | Me | MS m/z: 283(M + Na)+<br>1H NMR(200 MHz, CDCl3) δ (ppm):<br>1.61(d, J=6.4 Hz, 3H), 2.65-2.98 (m, 4H), 4.99-5.14(m, 1H), 6.68-6.80 (m, 2H), 7.23(s, 1H) |
| 62 | 8-OMe | H | Me | MS m/z: 283(M + Na)+<br>1H NMR (200 MHz, CDCl3) δ (ppm):<br>1.62(d, J=6.2Hz, 3H), 2.71-2.92(m, 4H), 3.82(s, 1H), 5.02-5.19(br, 1H), 6.67 (dd, J=2.6, 8.4 Hz, 1H), 7.10-7.14(m, 2H), 7.52(s, 1H) |

TABLE 9-2

| Example | R | R' | R" | Data |
|---|---|---|---|---|
| 63 | 6-OBzl | H | Me | MS m/z: 319(M−OH)+<br>1H NMR(300MHz, CDCl3) δ(ppm):<br>1.62(d, J=6.4Hz, 3H), 2.68-2.81(m, 2H), 2.93-3.07(m, 2H), 5.03-5.18(m, 3H), 6.79(s, 1H), 6.82(d, J=7.9Hz, 1H), 7.00(d, J=7.9Hz, 1H), 7.14(t, J=7.9Hz, 1H), 7.27-7.51(m, 5H) |
| 64 | 7-OBzl | H | Me | MS m/z: 319(M−OH)+<br>1H NMR(300MHz, CDCl3) δ(ppm):<br>1.61(d, J=6.6Hz, 3H), 2.53-3.15(m, 4H), 4.89-5.20(m, 3H), 6.65-6.92(m, 3H), 7.11-7.60(m, 6H) |
| 65 | 8-F | H | Me | MS m/z: 230(M−OH)+<br>1H NMR(200MHz, CDCl3) δ(ppm):<br>1.62(d, J=6.6Hz, 3H), 2.63-3.00(m, 4H), 4.89-5.21(m, 1H), 6.75-6.85(m, 2H), 6.97-7.16(m, 2H) |

TABLE 9-2-continued

| Example | R | R' | R" | Data |
|---|---|---|---|---|
| 66 | 7-F | 8-OMe | Me | MS m/z: 260(M−OH)+<br>¹H NMR(200MHz, CDCl₃) δ(ppm): 1.62(d, J=6.4Hz, 3H), 2.61-2.94(m, 4H), 3.91(s, 3H), 5.10(q, J=6.4Hz, 1H), 6.79(s, 1H), 6.85-7.03(m, 2H) |
| 67 | 6-Me | 8-Me | Et | MS m/z: 295(M+Na)+<br>¹H NMR(300MHz, CDCl₃) δ(ppm): 1.00(t, J=7.5Hz, 3H), 1.80-1.99(m, 3H), 2.28(s, 3H), 2.30(s, 3H), 2.70-2.91(m, 4H), 4.72-4.85(m, 1H), 6.78(s, 1H), 6.85(s, 1H), 7.03(s, 1H) |

TABLE 9-3

| Example | R | R' | R" | Data |
|---|---|---|---|---|
| 68 | 6-Me | 8-Me | Pr | MS m/z: 309(M+Na)+<br>¹H NMR(300MHz, CDCl₃) δ(ppm): 0.97(t, J=7.5Hz, 3H), 1.32-1.54(m, 2H), 1.72-1.99(m, 3H), 2.28(s, 3H), 2.30(s, 3H), 2.68-2.90(m, 4H), 4.80-4.93(m, 1H), 6.77(s, 1H), 6.85(s, 1H), 7.03(s, 1H) |
| 69 | 6-Me | 8-Me | Prⁱ | MS m/z: 309(M+Na)+<br>1H NMR(300MHz, CDCl₃) δ(ppm): 0.92(d, J=6.8Hz, 3H) 1.07(d, J=6.7Hz, 3H) 1.89-2.10(m, 3H) 2.28(s, 3H) 2.29(s, 3H) 2.67-2.91(m, 4H) 4.51-4.60(m, 1H) 6.75(s, 1H) 6.84(s, 1H) 7.03(s, 1H) |
| 70 | 8-Et | H | Me | MS m/z: 281(M+Na)+<br>1H NMR(300MHz, CDCl₃) δ(ppm): 1.25(t, J=7.6Hz, 3H) 1.62(d, J=6.4Hz, 3H) 1.91-1.95(m, 1H) 2.63(q, J=7.6Hz, 2H) 2.72-2.94(m, 4H) 5.04-5.15(m, 1H) 6.79(s, 1H) 6.98(d, J=7.5Hz, 1H) 7.11(d, J=7.5Hz, 1H) 7.16(s, 1H) |
| 71 | 8-Pr | H | Me | MS m/z: 295(M+Na)+<br>1H NMR(300MHz, CDCl₃) δ(ppm): 0.96(t, J=7.3Hz, 3H) 1.58-1.74(m, 5H) 1.89-1.97(m, 1H) 2.57(t, J=7.5Hz, 2H) 2.71-2.94(m, 4H) 5.02-5.18(m, 1H) 6.79(s, 1H) 6.95(d, J=7.6Hz, 1H) 7.10(d, J=7.6Hz, 1H) 7.13(s, 1H) |

TABLE 9-4

| Example | R | R' | R" | Data |
|---|---|---|---|---|
| 72 | 8-Prⁱ | H | Me | MS m/z: 295(M+Na)+<br>1H NMR(300MHz, CDCl₃) δ(ppm): 1.26(d, J=7.0Hz, 6H) 1.62(d, J=6.3Hz, 3H) 1.94(br s, 1H) 2.70-2.95(m, 5H) 5.10(q, J=6.3Hz, 1H) 6.79(s, 1H) 7.01(d, J=7.5Hz, 1H) 7.12(d, J=7.5Hz, 1H) 7.18(s, 1H) |
| 73 | 8-cycloHexyl | H | Me | MS m/z: 335(M+Na)+<br>1H NMR(300MHz, CDCl₃) δ(ppm): 1.27-1.57(m, 5H) 1.62(d, J=6.5Hz, 3H) 1.69-1.97(m, 5H) 2.34-2.59(m, 1H) 2.66-2.97(m, 4H) 5.02-5.16(m, 1H) 6.79(s, 1H) 6.98(d, J=7.7Hz, 1H) 7.11(d, J=7.7Hz, 1H) 7.16(s, 1H) |
| 74 | 8-Cl | H | Me | MS m/z: 245(M−OH)+<br>¹H NMR(200MHz, CDCl₃) δ(ppm): 1.62(d, J=6.4Hz, 3H), 2.67-2.98(m, 4H), 5.10(q, J=6.4Hz, 1H), 6.80(s, 1H), 7.01-7.18(m, 2H), 7.26-7.31(m, 1H) |
| 75 | 7-Me | 8-OMe | Me | MS m/z: 297(M+Na)+<br>1H NMR(300MHz, CDCl₃) δ(ppm): 1.62(d, J=6.4Hz, 3H), 1.93(d, J=4.5Hz, 1H), 2.20(s, 3H), 2.68-2.88(m, 4H)m 3.86(s, 3H)m 5.03-5.16(m, 1H) m6.79(s, 2H) m6.96(s, 1H) |
| 76 | 6-F | 8-Me | Me | MS m/z: 245(M−OH)+<br>¹H NMR(200MHz, CDCl₃) δ(ppm): 1.62(d, J=6.6Hz, 3H), 2.32(s, 3H), 2.63-3.01(m, 4H), 4.88-5.21(m, 1H), 6.71(d, J=11.0Hz, 1H), 6.79(s, 1H), 6.93(s, 1H) |

TABLE 9-5

| Example | R | R' | R" | Data |
|---|---|---|---|---|
| 77 | 7-F | 8-Me | Me | MS m/z: 245(M−OH)$^+$<br>$^1$H NMR(200MHz, CDCl$_3$) δ(ppm):<br>1.62(d, J=6.6Hz, 3H), 2.26(s, 6H),<br>2.70-2.91(m, 4H), 4.78-5.33(m, 1H), 6.78(s, 1H),<br>6.85(d, J=10.1Hz, 1H), 7.11(d, J=7.5Hz, 1H) |
| 78 | 6-F | 8-OMe | Me | MS m/z: 301(M+Na)$^+$<br>$^1$H NMR(200MHz, CDCl$_3$) δ(ppm):<br>1.62(d, J=6.2Hz, 3H), 2.65-3.01(m, 4H),<br>3.81(s, 3H), 5.10(q, J=6.2Hz, 1H), 6.47(dd,<br>J=11.0, 2.2z, 1H), 6.68(d, J=2.2Hz, 1H),<br>6.80(s, 1H) |
| 79 | 7-F | H | Me | MS m/z: 231(M−OH)$^+$<br>$^1$H NMR(200MHz, CDCl$_3$) δ(ppm):<br>1.62(d, J=6.2Hz, 3H), 2.72-2.97(m, 4H),<br>5.09(q, J=6.2Hz, 1H), 6.73-6.99(m, 3H),<br>7.17-7.33(m, 1H) |
| 80 | 7-Cl | H | Me | MS m/z: 247(M−OH)$^+$<br>$^1$H NMR(200MHz, CDCl$_3$) δ(ppm):<br>1.62(d, J=6.3Hz, 3H), 2.62-3.03(m, 4H),<br>5.09(q, J=6.3Hz, 1H), 6.79(s, 1H), 7.02-7.49(m, 3H) |
| 81 | 7-Me | H | Me | MS m/z: 227(M−OH)$^+$<br>$^1$H NMR(200MHz, CDCl$_3$) δ(ppm):<br>1.62(d, J=6.6Hz, 3H), 2.32(s, 3H),<br>2.62-3.06(m, 4H), 4.89-5.27(m, 1H), 6.78(s, 1H),<br>6.94-7.08(m, 2H), 7.12-7.31(m, 1H) |

TABLE 9-6

| Example | R | R' | R" | Data |
|---|---|---|---|---|
| 82 | 7-OEt | H | Me | MS m/z: 297(M+Na)$^+$<br>1H NMR(300MHz, CDCl$_3$) δ(ppm):<br>1.41(t, J=7.0Hz, 3H)1.61(d, J=6.4Hz, 3H)<br>1.91(d, J=4.2Hz, 1H)2.68-2.94(m, 4H)<br>4.04(q, J=7.0Hz, 2H)4.99-5.15(m, 1H)<br>6.66-6.79(m, 3H)7.23(d, J=8.2Hz, 1H) |
| 83 | 7-O-cycloHexylmethyl | H | Me | MS m/z: 365(M+Na)$^+$<br>1H NMR(300MHz, CDCl$_3$) δ(ppm):<br>0.97-1.40(m, 5H), 1.61(d, J=6.5Hz, 2H),<br>1.65-1.93(m, 7H), 2.66-2.96(m, 4H), 3.75(d,<br>J=6.2Hz, 2H), 5.01-5.14(m, 1H),<br>6.68-6.79(m, 3H), 7.23(d, J=8.1Hz, 1H) |
| 84 | 7-OPr | H | Me | MS m/z: 311(M+Na)$^+$<br>1H NMR(300MHz, CDCl$_3$) δ(ppm):<br>1.04(t, J=7.5Hz, 3H), 1.61(d, J=6.4Hz, 3H),<br>1.74-1.87(m, 2H), 1.91(br s, 1H),<br>2.70-2.94(m, 4H), 3.93(t, J=6.5Hz, 2H),<br>5.08(q, J=6.0Hz, 1H), 6.67-6.80(m, 3H),<br>7.23(d, J=8.1Hz, 1H) |
| 85 | 7-OPr$^i$ | H | Me | MS m/z: 311(M+Na)$^+$<br>1H NMR(300MHz, CDCl$_3$) δ(ppm):<br>1.34(d, J=6.1Hz, 6H), 1.61(d, J=6.4Hz, 3H),<br>1.92(br s, 1H), 2.69-2.94(m, 4H),<br>4.47-4.62(m, 1H), 5.02-5.13(m, 1H),<br>6.67-6.79(m, 3H), 7.22(d, J=8.2Hz, 1H) |

TABLE 9-7

| Example | R | R' | R" | Data |
|---|---|---|---|---|
| 86 | 7-OH | H | Me | MS m/z: 269(M+Na)$^+$<br>1HNMR(300MHz, dmso-d6) δ(ppm):<br>1.41(d, J=6.4Hz, 3H)2.56-2.88(m, 4H)<br>4.62-5.05(m, 1H)5.46(m, 1H)6.60(dd,<br>J=8.2, 2.6Hz, 1H)6.65(d, J=2.6Hz, 1H)<br>6.73(d, J=0.9Hz, 1H)7.06(d, J=8.2Hz, 1H)<br>9.40(br s, 1H) |
| 87 | 7-NMe$_2$ | H | Me | MS m/z: 274(M+H)$^+$<br>$^1$H NMR(200MHz, CDCl$_3$) δ(ppm):<br>1.61(d, J=6.2Hz, 3H), 2.59-3.13(m, 4H),<br>2.96(s, 6H), 4.81-5.24(m, 1H)<br>6.46-6.71(m, 2H)6.76(s, 1H)7.21(d,<br>J=9.2Hz, 1H) |
| 88 | 7-NHMe | H | Me | MS m/z: 260(M+H)$^+$<br>$^1$H NMR(200MHz, CDCl$_3$) δ(ppm):<br>1.61(d, J=6.6Hz, 3H), 2.60-3.02(m, 7H),<br>4.91-5.17(m, 1H), 6.38-6.57(m, 2H),<br>6.75(s, 1H), 7.17(d, J=8.8Hz, 1H) |
| 89 | 7-NHPr | H | Me | MS m/z: 288(M+H)$^+$<br>$^1$H NMR(200MHz, CDCl$_3$) δ(ppm): |

TABLE 9-7-continued

| Example | R | R' | R" | Data |
|---|---|---|---|---|
| 90 | 7-NHAc | H | Me | 1.00(t, J=7.1Hz, 3H), 1.55-1.75(m, 5H), 2.63-2.95(m, 4H), 3.10(t, J=7.1Hz, 2H), 5.06(q, J=6.4Hz, 1H), 6.35-6.57(m, 2H), 6.74(s, 1H), 7.15(d, J=8.8Hz, 1H) MS m/z: 288(M+H)⁺ $^1$H NMR(200MHz, CDCl$_3$) δ(ppm): 1.62(d, J=6.2Hz, 3H), 2.18(s, 3H), 2.65-3.05(m, 4H), 6.78(s, 1H), 7.02-7.17(m, 1H), 7.18-7.34(m, 2H), 7.38-7.54(m, 1H) |

TABLE 9-8

| Example | R | R' | R" | Data |
|---|---|---|---|---|
| 91 | 7-OBu | H | Me | MS m/z: 325(M + Na)⁺ $^1$H NMR (300 MHz, CDCl$_3$) δ (ppm): 0.98 (t, J=7.3Hz, 3 H), 1.35-1.68(m, 2H), 1.61(d, J=6.6Hz, 3H), 1.68-1.88(m, 2H), 2.59-3.03(m, 4H), 3.96(t, J=6.4 Hz, 2H), 5.03-5.12(m, 1H), 6.63-6.83(m, 3H), 7.22(d, J=7.9Hz, 1H) |
| 92 | 7-OBu$^i$ | H | Me | MS m/z: 325(M + Na)⁺ 1H NMR (300 MHz, CDCl$_3$) δ (ppm): 1.03(d, J=6.7Hz, 6H), 1.61(d, J=6.5 Hz, 3H), 1.92(br s, 1H), 2.00-2.16 (m, 1H), 2.68-2.95(m, 4H), 3.72(d, J=6.5 Hz, 2H), 4.97-5.18(m, 1H), 6.64-6.80 (m, 3H), 7.23(d, J=8.2Hz, 1H) |
| 93 | 7-O-Pentyl | H | Me | MS m/z: 339 (M + Na)⁺ $^1$H NMR (200 MHz, CDCl$_3$) δ (ppm): 0.94(t, J=7.0Hz, 3H), 1.31-1.54(m, 4H), 1.61(d, J=6.6Hz, 3H), 1.68-1.89(m, 2H), 2.65-3.01(m, 4H), 3.95(t, J=6.6Hz, 2H), 4.89-5.24(m, 1H), 6.61-6.88(m, 3H), 7.23(d, J=7.9Hz, 1H) |
| 94 | 7-O-cyclopropylmethyl | H | Me | MS m/z : 283(M − OH)⁺ 1 H NMR (300 MHz, CDCl$_3$) δ (ppm): 0.32-0.38(m, 2H)0.62-0.68(m, 2H)1.23-1.32(m, 1 H)1.61(d, J=6.3Hz, 3H) 1.90(br s, 1H)2.72-2.92(m, 4H)3.80 (d, J=6.9Hz, 2H)5.06-5.10(m, 1H) 6.71 6.77(m, 3H)7.23(d, J=8.1Hz, 1H) |

TABLE 9-9

| Example | R | R' | R" | Data |
|---|---|---|---|---|
| 95 | 7-O-cyclopentyl | H | Me | MS m/z: 337(M + Na)⁺ $^1$H NMR(300 MHz, CDCl$_3$) δ (ppm): 1.44-1.98(m, 8H), 1.61(d, J=6.2 Hz, 3H), 2.53-3.06(m, 4H), 4.64-4.91(m, 1H), 4.94-5.25(m, 1H), 6.54-6.90(m, 3H), 7.22(d, J=8.8 Hz, 1H) |
| 96 | 7-O-neopentyl | H | Me | MS m/z: 299(M − OH)⁺ $^1$H NMR(200 MHz, CDCl$_3$) δ (ppm): 1.03(s, 9H), 1.61(d, J=6.4 Hz, 3H), 2.64-2.98(m, 4H), 3.59(s, 3H), 5.07(q, J=6.4 Hz, 1H), 6.67-6.82(m, 2H), 7.22(d, J=7.9 Hz, 1H) |
| 97 | 7-O-allyl | H | Me | MS m/z: 269(M − OH)⁺ $^1$H NMR(300 MHz, CDCl$_3$) δ (ppm): 1.61(d, J=6.5 Hz, 3H) 1.92(d, J=4.5 Hz, 1H) 2.70-2.94(m, 4H) 4.50-4.57(m, 2H) 5.02-5.14(m, 1H) 5.25-5.33 (m, 1H) 5.36-5.47(m, 1H) 5.99-6.14(m, 1H) 6.72-6.80(m, 3H) 7.23(d, J=8.2 Hz, 1H) |
| 98 | 7-O-methallyl | H | Me | MS m/z: 323(M + Na)⁺ $^1$H NMR(300 MHz, CDCl$_3$) δ (ppm): 1.61(d, J=6.34 Hz, 3H), 1.84(s, 3H), 1.91(d, J=4.5 Hz, 1H), 2.69-2.96 (m, 4H), 4.44(s, 2H), 4.95-5.13(m, 3H), 6.71-6.80(m, 3H), 7.23(d, J=8.2 Hz, 1H |

TABLE 9-10

| Example | R | R' | R" | Data |
|---|---|---|---|---|
| 99 | 7-O-CH2-C≡CH | H | Me | MS m/z: 307(M + Na)+<br>1H NMR(300 MHz, CDCl3) δ (ppm):<br>1.61(d, J=6.5 Hz, 3H), 1.93(d, J=4.5 Hz, 1H), 2.53(t, J=2.4 Hz, 1H), 2.70-2.98(m, 4H), 4.69(d, J=2.4 Hz, 2H), 4.98-5.15(m, 1H), 6.72-6.86(m, 3H), 7.20-7.29(m, 1H) |
| 100 | 8-OEt | H | Me | MS m/z: 297(M + Na)+<br>1H NMR(200 MHz, CDCl3) δ (ppm):<br>1.42(t, J=6.9 Hz, 3H), 1.62(d, J=6.5 Hz, 3H), 2.58-2.97(m, 4H), 4.04(q, J=6.9 Hz, 2H), 5.09(q, J=6.5 Hz, 1H), 6.67(dd, J=8.4, 2.4 Hz, 1H), 6.79(s, 1H), 6.87(d, J=2.4 Hz, 1H) 7.08(d, J=8.4 Hz, 1H) |
| 101 | 8-OBzl | H | Me | MS m/z: 359(M + Na)+<br>1H NMR(200 MHz, CDCl3) δ (ppm):<br>1.62(d, J=6.2 Hz, 3H), 2.67-2.96(m, 4H), 5.01-5.16(m, 3H), 6.74(dd, J=8.2, 2.6 Hz, 1H), 6.79(s, 1H), 6.97 (d, J=2.6 Hz, 4H), 7.09(d, J=8.2 Hz, 1H), 7.26-7.50(m, 5H) |
| 102 | 7-Bu | H | Me | MS m/z: 258(M + Na)+<br>1H NMR(200 MHz, CDCl3) δ (ppm):<br>0.93(t, J=7.3 Hz, 3H), 1.27-1.48 (m, 2H), 1.49-1.72(m, 5H), 2.50-2.65(t, J=7.5 Hz, 2H), 2.69-3.01(m, 4H), 4.96-5.23 (m, 1H), 6.78(s, 1H), 6.90-7.10(m, 2H), 7.23(m, 1H) |

TABLE 9-11

| Example | R | R' | R" | Data |
|---|---|---|---|---|
| 103 | 7-Pr | H | Me | MS m/z: 255(M−OH)+<br>1H NMR(200MHz, CDCl3) δ(ppm):<br>0.95(t, J=7.3Hz, 3H), 1.47-1.79(m, 5H), 2.55(t, J=7.5Hz, 2H), 5.08(q, J=6.6Hz, 1H), 6.78(s, 1H), 6.93-7.08(m, 2H), 7.23(d, J=9.7Hz, 1H) |
| 104 | 7-Et | H | Me | MS m/z: 241(M−OH)+<br>1H NMR(200MHz, CDCl3) δ(ppm):<br>1.24(t, J=7.7Hz, 3H), 1.62(d, J=6.4Hz, 3H), 2.62(q, J=7.7Hz, 2H), 2.69-3.01(m, 4H), 5.08(q, J=6.4Hz, 1H), 6.78(s, 1H), 6.95-7.12(m, 2H), 7.24(d, J=8.4Hz, 1H) |

Test Example

Male KKAy mice (11 to 12 weeks old) (each n=6) were used as a model for type 2 diabetes. 11% sulfobutyl ether-β-cyclodextrin was added to the compounds of Examples 1 and 59, and these products were administered subcutaneously in a dose of 3 mg/5 mL/kg, twice a day, continuously for 2 weeks. A group that was given just the vehicle was used as a control group, and male C57BL/6J mice (11 to 12 weeks old) (n=6) that had similarly been given the vehicle were used for a healthy group. The livers were collected, and a Triglyceride E Test Wako (Wako Pure Chemicals) was used to quantify the triglyceride content in the liver. These results are given in Table 10 (in the table, an asterisk means P<0.05, and a double asterisk means P<0.01). Blood was also sampled from the orbital venous plexus, and the glucose level in the separated serum was quantified by enzyme method using a L-type Wako GLU2 (Wako Pure Chemicals). These results are given in Table 11 (in the table, a double asterisk means P<0.01).

TABLE 10

| | Triglyceride content in liver (mg/g liver) |
|---|---|
| Control group | 61.7 |
| Example 1 | 47.5* |
| Example 59 | 34.8** |
| Healthy group | 12.5 |

TABLE 11

| | Blood glucose level (mg/dL) |
|---|---|
| Control group | 532 |
| Example 1 | 491 |
| Example 59 | 269** |
| Healthy group | 211 |

Thus, it was shown that the compound of the present invention significantly lowered the triglyceride level in the liver as compared to the control group, and lowered the glucose level in serum. Therefore, the compound of the present invention is useful as a drug for preventing or treating diabetes, hyperlipidemia, fatty liver, obesity, impaired glucose tolerance, diabetes complications (such as kidney disease, neuropathy, and retinopathy), metabolic syndrome, and syndrome X.

The invention claimed is:

1. A 4,5-dihydronaphtho[1,2-b]thiophene derivative expressed by the formula:

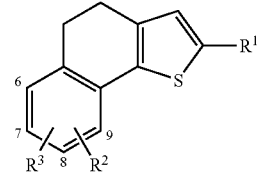

(wherein $R^1$ is a $C_1$ to $C_{10}$ 1-hydroxyalkyl group or a $C_1$ to $C_{10}$ acyl group, and $R^2$ and $R^3$ separately substitute in the 6-, 7-, 8-, or 9-positions, and are each independently a hydrogen atom, a halogen atom, a $C_1$ to $C_{10}$ alkyl group, a hydroxy group, a $C_1$ to $C_{10}$ alkoxy group, a $C_1$ to $C_5$ alkenyloxy group, a $C_1$ to $C_5$ alkynyloxy group, a benzyloxy group, a nitro group, an acetyl group, or a group expressed by the formula —$NR^4R^5$ (wherein $R^4$ and $R^5$ are each independently a hydrogen atom, an acetyl group, a trifluoroacetyl group, a $C_1$ to $C_{10}$ alkyl group, or a benzyl group), or $R^2$ and $R^3$ are bonded together to form an ethylenedioxy group, provided that when $R^1$ is an acyl group and $R^2$ is a hydrogen atom, then $R^3$ is neither a hydrogen atom nor an acetyl.

2. The 4,5-dihydronaphtho[1,2-b]thiophene derivative or pharmaceutically acceptable salt thereof according to claim 1, wherein $R^1$ is a 1-hydroxyethyl group, and $R^2$ and $R^3$ are each independently a hydrogen atom, a halogen atom, a $C_1$ to $C_{10}$ alkyl group, a hydroxy group, a $C_1$ to $C_{10}$ alkoxy group, a $C_1$ to $C_5$ alkenyloxy group, a $C_1$ to $C_5$ alkynyloxy group, a benzyloxy group, a nitro group, an acetyl group, or a group expressed by the formula —$NR^4R^5$ (wherein $R^4$ and $R^5$ are each independently a hydrogen atom, an acetyl group, a trifluoroacetyl group, a $C_1$ to $C_{10}$ alkyl group, or a benzyl group), or $R^2$ and $R^3$ are bonded together to form an ethylenedioxy group.

3. The 4,5-dihydronaphtho[1,2-b]thiophene derivative or pharmaceutically acceptable salt thereof according to claim 1, wherein $R^1$ is an acetyl group, $R^2$ is a halogen atom, a $C_1$ to $C_{10}$ alkyl group, a hydroxy group, a $C_1$ to $C_{10}$ alkoxy group, a $C_1$ to $C_5$ alkenyloxy group, a $C_1$ to $C_5$ alkynyloxy group, a benzyloxy group, a nitro group, or a group expressed by the formula —$NR^4R^5$ (wherein $R^4$ and $R^5$ are each independently a hydrogen atom, an acetyl group, a trifluoroacetyl group, a $C_1$ to $C_{10}$ alkyl group, or a benzyl group), and $R^3$ is a hydrogen atom, a halogen atom, a $C_1$ to $C_{10}$ alkyl group, a $C_1$ to $C_5$ alkenyl group, a $C_1$ to $C_5$ alkynyl group, a hydroxy group, a $C_1$ to $C_{10}$ alkoxy group, a benzyloxy group, a nitro group, or a group expressed by the formula —$NR^6R^7$ (wherein $R^6$ and $R^7$ are each independently a hydrogen atom, an acetyl group, a trifluoroacetyl group, a $C_1$ to $C_{10}$ alkyl group, or a benzyl group), or $R^2$ and $R^3$ are bonded together to form an ethylenedioxy group.

4. The 4,5-dihydronaphtho[1,2-b]thiophene derivative or pharmaceutically acceptable salt thereof according to claim 2, wherein $R^1$ is a 1-hydroxyethyl group and $R^2$ and $R^3$ are each independently a $C_1$ to $C_{10}$ alkyl group or a $C_1$ to $C_{10}$ alkoxy group.

5. The 4,5-dihydronaphtho[1,2-b]thiophene derivative or pharmaceutically acceptable salt thereof according to claim 3, wherein $R^1$ is an acetyl group and $R^2$ and $R^3$ are each independently a $C_1$ to $C_{10}$ alkyl group or a $C_1$ to $C_{10}$ alkoxy group.

6. A pharmaceutical composition comprising the 4,5-dihydronaphtho[1,2-b]thiophene derivative or pharmaceutically acceptable salt thereof according to any one of claims 1 to 5.

7. A hypotriglyceridemic agent whose active ingredient is the 4,5-dihydronaphtho[1,2-b]thiophene derivative or pharmaceutically acceptable salt thereof according to any one of claims 1 to 5.

8. A hypoglycemic agent whose active ingredient is the 4,5-dihydronaphtho[1,2-b]thiophene derivative or pharmaceutically acceptable salt thereof according to any one of claims 1 to 5.

9. An agent for treating diabetes, hyperlipidemia, fatty liver, obesity, impaired glucose tolerance, diabetes complications, metabolic syndrome, and syndrome X, whose active ingredient is the 4,5-dihydronaphtho[1,2-b]thiophene derivative or pharmaceutically acceptable salt thereof according to any one of claims 1 to 5.

* * * * *

UNITED STATES PATENT AND TRADEMARK OFFICE
CERTIFICATE OF CORRECTION

PATENT NO. : 7,384,974 B2  Page 1 of 1
APPLICATION NO. : 10/566572
DATED : June 10, 2008
INVENTOR(S) : Minoru Taguchi, Ryo Suzuki and Ayako Mikami It is certified that error appears in the above-identified patent and that said Letters Patent is hereby corrected as shown below:

Title Page item 73 please correct the Assignee's name:

Delete "Taisha" and insert --Taisho--.

Signed and Sealed this

Seventh Day of October, 2008

JON W. DUDAS
*Director of the United States Patent and Trademark Office*